(12) United States Patent
Lopez et al.

(10) Patent No.: US 11,744,443 B2
(45) Date of Patent: Sep. 5, 2023

(54) LAYERED WALLS FOR RIGIDIZING DEVICES

(71) Applicant: NEPTUNE MEDICAL INC., Burlingame, CA (US)

(72) Inventors: Francisco G. Lopez, San Mateo, CA (US); Garrett J. Gomes, Pleasant Hill, CA (US); Alexander Q. Tilson, Burlingame, CA (US)

(73) Assignee: NEPTUNE MEDICAL INC., Burlingame, CA (US)

( * ) Notice: Subject to any disclaimer, the term of this patent is extended or adjusted under 35 U.S.C. 154(b) by 0 days.

(21) Appl. No.: 17/995,294

(22) PCT Filed: Mar. 29, 2021

(86) PCT No.: PCT/US2021/024582
§ 371 (c)(1),
(2) Date: Sep. 30, 2022

(87) PCT Pub. No.: WO2021/202336
PCT Pub. Date: Oct. 7, 2021

(65) Prior Publication Data
US 2023/0120269 A1  Apr. 20, 2023

Related U.S. Application Data

(60) Provisional application No. 63/030,235, filed on May 26, 2020, provisional application No. 63/002,202, filed on Mar. 30, 2020.

(51) Int. Cl.
*A61B 1/00*    (2006.01)
*A61M 25/00*   (2006.01)
(Continued)

(52) U.S. Cl.
CPC ........ *A61B 1/00078* (2013.01); *A61B 1/0055* (2013.01); *A61M 25/005* (2013.01); *A61M 25/0045* (2013.01); *A61M 25/0155* (2013.01)

(58) Field of Classification Search
CPC .............. A61B 1/00078; A61B 1/0055; A61B 1/00135; A61M 25/0045; A61M 25/005
See application file for complete search history.

(56) References Cited

U.S. PATENT DOCUMENTS 2,268,321 A   12/1941 Flynn
2,767,705 A   10/1956 Moore
(Continued)

FOREIGN PATENT DOCUMENTS

AU    2013207571 B1   8/2013
CN       2613655 Y    4/2004
(Continued)

OTHER PUBLICATIONS

Entrada® colonic overtuube product brochure downloaded from internet http://www.usendoscopy.com/~/media/Files/Documents/Spec-Sheet-International/760358c_entrada_intl_ss_web.pdf Accessed Date: Jun. 5, 2017 (the year of publication is sufficiently earlier than the effective U.S. filing date and any foreign priority date so that the particular month of publication is not in issue) 2009.
(Continued)

*Primary Examiner* — Lau A Bouchelle
*Assistant Examiner* — John A Doubrava
(74) *Attorney, Agent, or Firm* — Shay Glenn LLP

(57) ABSTRACT

A rigidizing device includes an elongate flexible tube, a stiffening layer positioned radially outwards of the elongate flexible tube, an outer layer over the elongate flexible tube and the stiffening layer, and a vacuum or pressure inlet between the elongate flexible tube and the outer layer and configured to attach to a source of vacuum or pressure. The
(Continued)

elongate flexible tube includes a first reinforcement element and a second reinforcement element. The second reinforcement element is counterwound relative to the first reinforcement element. The rigidizing device is configured to have a rigid configuration when vacuum or pressure is applied through the inlet and a flexible configuration when vacuum or pressure is not applied through the inlet.

17 Claims, 27 Drawing Sheets

(51) Int. Cl.
  *A61B 1/005* (2006.01)
  *A61M 25/01* (2006.01)

(56) References Cited

U.S. PATENT DOCUMENTS

| | | | |
|---|---|---|---|
| 3,859,986 A | 1/1975 | Okada et al. |
| 3,998,216 A | 12/1976 | Hosono |
| 4,066,071 A | 1/1978 | Nagel |
| 4,141,364 A | 2/1979 | Schultze |
| 4,151,800 A | 5/1979 | Dotts et al. |
| 4,176,662 A | 12/1979 | Frazer |
| 4,425,919 A | 1/1984 | Alston, Jr. |
| 4,551,140 A | 11/1985 | Shinohara |
| 4,690,131 A | 9/1987 | Lyddy, Jr. et al. |
| 4,696,544 A | 9/1987 | Costella |
| 4,717,379 A | 1/1988 | Ekholmer |
| 4,794,412 A | 12/1988 | Casey et al. |
| 4,794,912 A | 1/1989 | Lia |
| 4,815,450 A | 3/1989 | Patel |
| 4,817,613 A | 4/1989 | Jaraczewski et al. |
| 4,893,613 A | 1/1990 | Hake |
| 4,959,058 A | 9/1990 | Michelson |
| 4,961,738 A | 10/1990 | Mackin |
| 5,018,436 A | 5/1991 | Evangelista et al. |
| 5,019,121 A | 5/1991 | Krauter |
| 5,037,386 A | 8/1991 | Marcus et al. |
| 5,105,819 A | 4/1992 | Wollschlager et al. |
| 5,123,421 A | 6/1992 | Sinofsky |
| 5,174,276 A | 12/1992 | Crockard |
| 5,188,595 A | 2/1993 | Jacobi |
| 5,251,611 A | 10/1993 | Zehel et al. |
| 5,337,733 A * | 8/1994 | Bauerfeind ........ A61B 1/00078 |
| | | | 604/524 |
| 5,496,292 A | 3/1996 | Burnham |
| 5,531,685 A | 7/1996 | Hemmer et al. |
| 5,531,719 A | 7/1996 | Takahashi |
| 5,577,992 A | 11/1996 | Chiba et al. |
| 5,601,588 A | 2/1997 | Tonomura et al. |
| 5,607,435 A | 3/1997 | Sachdeva et al. |
| 5,624,381 A | 4/1997 | Kieturakis |
| 5,632,734 A | 5/1997 | Gate et al. |
| 5,662,587 A | 9/1997 | Grundfest et al. |
| 5,662,621 A | 9/1997 | Lafontaine |
| 5,746,692 A | 5/1998 | Bacich et al. |
| 5,749,828 A | 5/1998 | Solomon et al. |
| 5,759,151 A | 6/1998 | Sturges |
| 5,779,624 A | 7/1998 | Chang |
| 5,782,811 A | 7/1998 | Samson et al. |
| 5,823,961 A | 10/1998 | Fields et al. |
| 5,882,347 A | 3/1999 | Laan et al. |
| 5,891,112 A | 4/1999 | Samson |
| 5,906,591 A | 5/1999 | Dario et al. |
| 5,916,145 A | 6/1999 | Chu et al. |
| 5,916,147 A | 6/1999 | Boury |
| 5,951,539 A | 9/1999 | Nita et al. |
| 5,976,074 A | 11/1999 | Moriyama |
| 6,090,099 A | 7/2000 | Samson et al. |
| 6,159,187 A | 12/2000 | Park et al. |
| 6,162,171 A | 12/2000 | Ng et al. |
| 6,179,776 B1 | 1/2001 | Adams et al. |
| 6,190,357 B1 | 2/2001 | Ferrari et al. |
| 6,217,565 B1 | 4/2001 | Cohen |
| 6,296,644 B1 | 10/2001 | Surat et al. |
| 6,309,346 B1 | 10/2001 | Farhadi |
| 6,364,878 B1 | 4/2002 | Hall |
| 6,368,315 B1 | 4/2002 | Gillis et al. |
| 6,468,203 B2 | 10/2002 | Beison |
| 6,485,409 B1 | 11/2002 | Voloshin et al. |
| 6,503,225 B1 | 1/2003 | Kirsch et al. |
| 6,517,477 B1 | 2/2003 | Wendlandt |
| 6,547,724 B1 | 4/2003 | Soble |
| 6,572,538 B2 | 6/2003 | Takase |
| 6,572,590 B1 | 6/2003 | Stevens et al. |
| 6,579,277 B1 | 6/2003 | Rabiner et al. |
| 6,610,007 B2 | 8/2003 | Belson et al. |
| 6,612,982 B1 | 9/2003 | Ouchi |
| 6,616,628 B2 | 9/2003 | Hayzelden |
| 6,620,126 B2 | 9/2003 | Unsworth et al. |
| 6,623,424 B2 | 9/2003 | Hayakawa et al. |
| 6,712,832 B2 | 3/2004 | Shah |
| 6,726,677 B1 | 4/2004 | Flaherty et al. |
| 6,730,020 B2 | 5/2004 | Peng et al. |
| 6,780,151 B2 | 8/2004 | Grabover et al. |
| 6,783,491 B2 | 8/2004 | Saadat et al. |
| 6,790,173 B2 | 9/2004 | Saadat et al. |
| 6,793,621 B2 | 9/2004 | Butler et al. |
| 6,793,661 B2 | 9/2004 | Hamilton et al. |
| 6,800,056 B2 | 10/2004 | Tartaglia et al. |
| 6,869,393 B2 | 3/2005 | Buller |
| 6,899,673 B2 | 5/2005 | Ogura et al. |
| 6,911,004 B2 | 6/2005 | Kim et al. |
| 6,923,754 B2 | 8/2005 | Lubock |
| 6,960,162 B2 | 11/2005 | Saadat et al. |
| 6,974,411 B2 | 12/2005 | Belson |
| 6,984,203 B2 | 1/2006 | Tartaglia et al. |
| 7,060,199 B2 | 6/2006 | Woydt et al. |
| 7,172,552 B2 | 2/2007 | Wendlandt |
| 7,214,230 B2 | 5/2007 | Brock et al. |
| 7,288,101 B2 | 10/2007 | Deem et al. |
| 7,291,127 B2 | 11/2007 | Eidenschink |
| 7,365,509 B2 | 4/2008 | Park et al. |
| 7,438,712 B2 | 10/2008 | Chouinard |
| 7,511,733 B2 | 3/2009 | Takizawa et al. |
| 7,537,562 B2 | 5/2009 | Takano |
| 7,559,916 B2 | 7/2009 | Smith et al. |
| 7,591,782 B2 | 9/2009 | Fujikura |
| 7,598,652 B2 | 10/2009 | Kornbluh et al. |
| 7,695,428 B2 | 4/2010 | Machida |
| 7,736,323 B2 | 6/2010 | Von Weymarn-Scharli |
| 7,749,196 B2 | 7/2010 | Osborne et al. |
| 7,837,615 B2 | 11/2010 | Le |
| 7,850,725 B2 | 12/2010 | Vardi et al. |
| 7,901,347 B2 | 3/2011 | Sekiguchi |
| 7,909,755 B2 | 3/2011 | Itoi |
| 7,918,819 B2 | 4/2011 | Karmarkar et al. |
| 7,918,845 B2 | 4/2011 | Saadat et al. |
| 7,931,661 B2 | 4/2011 | Saadat et al. |
| 7,935,047 B2 | 5/2011 | Yoshida et al. |
| 7,947,000 B2 | 5/2011 | Vargas et al. |
| 7,957,790 B2 | 6/2011 | Kleen |
| 7,970,455 B2 | 6/2011 | Zilberstein |
| 7,988,621 B2 | 8/2011 | Smith et al. |
| 8,047,236 B2 | 11/2011 | Perry |
| 8,075,476 B2 | 12/2011 | Vargas |
| 8,092,374 B2 | 1/2012 | Smith et al. |
| 8,109,953 B1 | 2/2012 | King, III et al. |
| 8,123,739 B2 | 2/2012 | McQueen et al. |
| 8,125,755 B2 * | 2/2012 | Garcia ..................... B25J 18/06 |
| | | | 361/233 |
| 8,192,422 B2 | 6/2012 | Zubiate et al. |
| 8,206,287 B2 | 6/2012 | Matsuo |
| 8,226,548 B2 | 7/2012 | Kucklick |
| 8,241,299 B2 | 8/2012 | Hibner |
| 8,246,575 B2 | 8/2012 | Viola |
| 8,257,257 B2 | 9/2012 | Takizawa et al. |
| 8,298,161 B2 | 10/2012 | Vargas |
| 8,313,014 B2 | 11/2012 | Bettuchi |
| 8,361,090 B2 | 1/2013 | Belson |
| 8,366,606 B2 | 2/2013 | Watanabe et al. |
| 8,388,519 B2 | 3/2013 | Garcia et al. |

(56) References Cited

U.S. PATENT DOCUMENTS

| | | |
|---|---|---|
| 8,439,825 B2 | 5/2013 | Sekiguchi |
| 8,460,179 B2 | 6/2013 | Ikeda et al. |
| 8,485,968 B2 | 7/2013 | Weimer et al. |
| 8,496,648 B2 | 7/2013 | Rogers |
| 8,506,479 B2 | 8/2013 | Piskun et al. |
| 8,517,923 B2 | 8/2013 | Belson et al. |
| 8,545,491 B2 | 10/2013 | Abboud et al. |
| 8,550,989 B2 | 10/2013 | Dohi et al. |
| 8,556,804 B2 | 10/2013 | Smith et al. |
| 8,663,096 B2 | 3/2014 | Viola |
| 8,663,196 B2 | 3/2014 | Kassab et al. |
| 8,708,894 B2 | 4/2014 | Smith et al. |
| 8,721,530 B2 | 5/2014 | Ohline et al. |
| 8,753,312 B2 | 6/2014 | Bowe et al. |
| 8,920,369 B2 | 12/2014 | Salahieh et al. |
| 8,969,639 B2 | 3/2015 | Xu et al. |
| 9,011,318 B2 | 4/2015 | Choset et al. |
| 9,066,655 B2 | 6/2015 | Stefanchik et al. |
| 9,114,228 B2 | 8/2015 | Zook et al. |
| 9,125,653 B2 | 9/2015 | Kovach |
| 9,155,451 B2 | 10/2015 | Smith et al. |
| 9,192,284 B2 | 11/2015 | Hirsch et al. |
| 9,192,288 B2 | 11/2015 | Okaniwa |
| 9,211,140 B2 | 12/2015 | Lauryssen et al. |
| 9,220,398 B2 | 12/2015 | Woodley et al. |
| 9,226,825 B2 | 1/2016 | Starksen et al. |
| 9,241,611 B2 | 1/2016 | Konno |
| 9,254,123 B2 | 2/2016 | Alvarez et al. |
| 9,295,511 B2 | 3/2016 | Smith et al. |
| 9,358,073 B2 | 6/2016 | Piligian et al. |
| 9,364,955 B2 | 6/2016 | Oyola et al. |
| 9,386,910 B2 | 7/2016 | West |
| 9,498,108 B1 | 11/2016 | Lombardi |
| 9,498,198 B2 | 11/2016 | Hu et al. |
| 9,505,125 B2 | 11/2016 | Zubiate et al. |
| 9,585,546 B2 | 3/2017 | Surti et al. |
| 9,610,068 B2 | 4/2017 | Kappel et al. |
| 9,649,473 B2 | 5/2017 | Gregorich et al. |
| 9,763,562 B2 | 9/2017 | Avitsian et al. |
| 9,814,372 B2 | 11/2017 | Smith et al. |
| 9,889,273 B2 * | 2/2018 | Cully ............. A61M 25/0102 |
| 9,913,570 B2 | 3/2018 | Kucharski et al. |
| 9,937,324 B2 | 4/2018 | Kim et al. |
| 10,092,291 B2 | 10/2018 | Voegele et al. |
| 10,307,042 B2 | 6/2019 | Lombardi |
| 10,463,495 B2 | 11/2019 | Rogers et al. |
| 11,122,971 B2 | 9/2021 | Tilson et al. |
| 11,135,398 B2 | 10/2021 | Tilson et al. |
| 11,219,351 B2 | 1/2022 | Tilson et al. |
| 11,478,608 B2 | 10/2022 | Tilson et al. |
| 11,554,248 B1 | 1/2023 | Tilson et al. |
| 2002/0107478 A1 | 8/2002 | Wendlandt |
| 2002/0161355 A1 | 10/2002 | Wollschlager |
| 2003/0023259 A1 | 1/2003 | Dubrul et al. |
| 2003/0083546 A1 | 5/2003 | Butler et al. |
| 2003/0153866 A1 | 8/2003 | Long et al. |
| 2003/0208220 A1 | 11/2003 | Worley et al. |
| 2003/0216691 A1 | 11/2003 | Jacobson |
| 2003/0225379 A1 | 12/2003 | Schaffer et al. |
| 2004/0019252 A1 | 1/2004 | Hirata |
| 2004/0044350 A1 | 3/2004 | Martin et al. |
| 2004/0092960 A1 | 5/2004 | Abrams et al. |
| 2004/0186349 A1 | 9/2004 | Ewers et al. |
| 2004/0186350 A1 | 9/2004 | Brenneman et al. |
| 2004/0243227 A1 | 12/2004 | Starksen et al. |
| 2004/0260236 A1 | 12/2004 | Manning et al. |
| 2005/0005363 A1 | 1/2005 | Giori et al. |
| 2005/0010237 A1 | 1/2005 | Niazi |
| 2005/0085829 A1 | 4/2005 | Kraemer et al. |
| 2005/0165275 A1 | 7/2005 | Von Felten et al. |
| 2005/0203340 A1 | 9/2005 | Butler et al. |
| 2005/0272974 A1 | 12/2005 | Iddan |
| 2005/0277966 A1 | 12/2005 | Ewers et al. |
| 2006/0041188 A1 | 2/2006 | Dirusso et al. |
| 2006/0047183 A1 | 3/2006 | Park |
| 2006/0058582 A1 | 3/2006 | Maahs et al. |
| 2006/0129130 A1 | 6/2006 | Tal et al. |
| 2006/0192465 A1 | 8/2006 | Kornbluh et al. |
| 2006/0258906 A1 | 11/2006 | Binmoeller |
| 2006/0264707 A1 | 11/2006 | Kinney |
| 2006/0287666 A1 | 12/2006 | Saadat et al. |
| 2007/0015965 A1 | 1/2007 | Cox et al. |
| 2007/0038025 A1 | 2/2007 | Yoshida |
| 2007/0045504 A1 | 3/2007 | Wollschlager |
| 2007/0088367 A1 | 4/2007 | Von Weymarn-Scharli |
| 2007/0100414 A1 | 5/2007 | Licata et al. |
| 2007/0106302 A1 | 5/2007 | Ortiz |
| 2007/0118015 A1 | 5/2007 | Wendiandt |
| 2007/0219411 A1 | 9/2007 | Dejima et al. |
| 2007/0239252 A1 | 10/2007 | Hopkins et al. |
| 2007/0250149 A1 | 10/2007 | Von Oepen et al. |
| 2007/0260121 A1 | 11/2007 | Bakos et al. |
| 2008/0051635 A1 | 2/2008 | Tanaka et al. |
| 2008/0058722 A1 | 3/2008 | Oepen et al. |
| 2008/0091073 A1 | 4/2008 | Park |
| 2008/0103440 A1 | 5/2008 | Ferren et al. |
| 2008/0139887 A1 | 6/2008 | Fitzpatrick |
| 2008/0172037 A1 | 7/2008 | Huang et al. |
| 2008/0188928 A1 | 8/2008 | Salahieh et al. |
| 2008/0200762 A1 | 8/2008 | Stokes et al. |
| 2008/0214893 A1 | 9/2008 | Tartaglia et al. |
| 2008/0234546 A1 | 9/2008 | Kawano et al. |
| 2008/0242928 A1 | 10/2008 | Kawano |
| 2008/0262300 A1 | 10/2008 | Ewers et al. |
| 2008/0275299 A1 | 11/2008 | Park |
| 2009/0048483 A1 | 2/2009 | Yamamoto |
| 2009/0062611 A1 | 3/2009 | Toyama |
| 2009/0062837 A1 | 3/2009 | Gasche et al. |
| 2009/0112063 A1 | 4/2009 | Bakos et al. |
| 2009/0131752 A1 | 5/2009 | Park |
| 2009/0157068 A1 | 6/2009 | Kallel et al. |
| 2009/0187163 A1 | 7/2009 | Uihlein |
| 2009/0240202 A1 | 9/2009 | Drasler et al. |
| 2009/0259200 A1 | 10/2009 | Lampropoulos et al. |
| 2009/0264704 A1 | 10/2009 | Shtul |
| 2010/0010308 A1 | 1/2010 | Braun et al. |
| 2010/0010437 A1 | 1/2010 | Miles et al. |
| 2010/0016663 A1 | 1/2010 | Maisch et al. |
| 2010/0069712 A1 | 3/2010 | Yamaya |
| 2010/0069716 A1 * | 3/2010 | Chin .................. A61B 1/0051 600/114 |
| 2010/0076451 A1 | 3/2010 | Zwolinski et al. |
| 2010/0087711 A1 | 4/2010 | Edwards |
| 2010/0137686 A1 | 6/2010 | Meron et al. |
| 2010/0145151 A1 | 6/2010 | Fukunaga et al. |
| 2010/0160735 A1 | 6/2010 | Bakos |
| 2010/0204546 A1 | 8/2010 | Hassidov et al. |
| 2010/0268025 A1 | 10/2010 | Belson |
| 2010/0331625 A1 | 12/2010 | Rosemurgy et al. |
| 2010/0331820 A1 | 12/2010 | Prisoo et al. |
| 2011/0015729 A1 | 1/2011 | Jimenez et al. |
| 2011/0040282 A1 | 2/2011 | Uihlein |
| 2011/0046442 A1 | 2/2011 | Matsushita |
| 2011/0049282 A1 | 3/2011 | Danielsson |
| 2011/0054253 A1 | 3/2011 | Jordá Albiñana et al. |
| 2011/0237888 A1 | 9/2011 | Matsushita |
| 2011/0245611 A1 | 10/2011 | Yeh et al. |
| 2011/0282149 A1 | 11/2011 | Vargas et al. |
| 2011/0306950 A1 | 12/2011 | Cucin |
| 2011/0319714 A1 | 12/2011 | Roelle et al. |
| 2012/0022329 A1 | 1/2012 | Wagh et al. |
| 2012/0041291 A1 | 2/2012 | Ferren et al. |
| 2012/0108902 A1 | 5/2012 | Frassica et al. |
| 2012/0130173 A1 | 5/2012 | Lutze |
| 2012/0143005 A1 | 6/2012 | Yeh et al. |
| 2012/0165607 A1 | 6/2012 | Ashida et al. |
| 2012/0165792 A1 | 6/2012 | Ortiz et al. |
| 2012/0172651 A1 | 7/2012 | Cutrer |
| 2012/0209062 A1 | 8/2012 | Qiao |
| 2012/0277528 A1 | 11/2012 | Qiao |
| 2012/0277729 A1 | 11/2012 | Melsheimer |
| 2013/0131641 A1 | 5/2013 | Jimenez et al. |
| 2013/0190565 A1 | 7/2013 | Gora et al. |
| 2013/0338440 A1 | 12/2013 | Sinai et al. |

(56) References Cited

U.S. PATENT DOCUMENTS

| | | | |
|---|---|---|---|
| 2014/0005683 | A1 | 1/2014 | Stand et al. |
| 2014/0081169 | A1 | 3/2014 | Gerding et al. |
| 2014/0088459 | A1 | 3/2014 | Roush et al. |
| 2014/0142393 | A1 | 5/2014 | Piskun et al. |
| 2014/0155702 | A1 | 6/2014 | Tilson et al. |
| 2014/0155783 | A1 | 6/2014 | Starksen et al. |
| 2014/0188054 | A1 | 7/2014 | Iijima et al. |
| 2014/0234600 | A1 | 8/2014 | Wang et al. |
| 2014/0243873 | A1 | 8/2014 | Franklin |
| 2014/0275860 | A1 | 9/2014 | Rottenberg |
| 2014/0276642 | A1 | 9/2014 | Cully et al. |
| 2014/0343358 | A1 | 11/2014 | Hameed et al. |
| 2014/0371764 | A1 | 12/2014 | Oyola et al. |
| 2015/0018616 | A1 | 1/2015 | Kumoyama |
| 2015/0038919 | A1 | 2/2015 | Bramwell et al. |
| 2015/0073216 | A1 | 3/2015 | Papay |
| 2015/0073409 | A1 | 3/2015 | Watson et al. |
| 2015/0094656 | A1 | 4/2015 | Salahieh et al. |
| 2015/0119640 | A1 | 4/2015 | Reydel |
| 2015/0133729 | A1 | 5/2015 | Reydel |
| 2015/0148602 | A1 | 5/2015 | Hill et al. |
| 2015/0148606 | A1 | 5/2015 | Rottenberg et al. |
| 2015/0164314 | A1 | 6/2015 | Peterson |
| 2015/0216589 | A1 | 8/2015 | Wittenberger et al. |
| 2015/0342608 | A1 | 12/2015 | Hernandez |
| 2015/0369325 | A1 | 12/2015 | Bureau et al. |
| 2016/0007832 | A1 | 1/2016 | Shimada |
| 2016/0066773 | A1 | 3/2016 | Cooper et al. |
| 2016/0096004 | A1 | 4/2016 | Gerrans et al. |
| 2016/0129547 | A1 | 5/2016 | Duescher et al. |
| 2016/0136393 | A1 | 5/2016 | Tsai et al. |
| 2016/0174829 | A1 | 6/2016 | Reydel |
| 2016/0198935 | A1 | 7/2016 | Choi et al. |
| 2016/0270870 | A1 | 9/2016 | Kowshik |
| 2016/0287059 | A1 | 10/2016 | Ha et al. |
| 2016/0324412 | A1 | 11/2016 | Hassidov et al. |
| 2017/0156567 | A1 | 6/2017 | Kaneko |
| 2017/0157363 | A1 | 6/2017 | Barrish et al. |
| 2017/0360281 | A1 | 12/2017 | Ponsky |
| 2018/0015257 | A1 | 1/2018 | Krolik et al. |
| 2018/0064366 | A1 | 3/2018 | Sweeney et al. |
| 2018/0132705 | A1 | 5/2018 | Higuchi |
| 2018/0184885 | A1 | 7/2018 | St. George |
| 2018/0249893 | A1 | 9/2018 | Yeung et al. |
| 2018/0263469 | A1 | 9/2018 | Okaniwa et al. |
| 2018/0264239 | A1 | 9/2018 | Piskun |
| 2018/0289925 | A1 | 10/2018 | Palmer et al. |
| 2018/0326197 | A1 | 11/2018 | McArthur et al. |
| 2018/0361116 | A1 | 12/2018 | Quick et al. |
| 2019/0226447 | A1 | 7/2019 | Stecher et al. |
| 2020/0030575 | A1 | 1/2020 | Bogusky et al. |
| 2020/0178763 | A1 | 6/2020 | Tilson et al. |
| 2020/0383677 | A1 | 12/2020 | Piligian et al. |
| 2021/0000505 | A1 | 1/2021 | Lenker et al. |
| 2021/0114507 | A1 | 4/2021 | Alexander et al. |
| 2021/0137366 | A1 | 5/2021 | Tilson et al. |
| 2022/0000355 | A1 | 1/2022 | Tilson et al. |
| 2022/0104690 | A1 | 4/2022 | Tilson et al. |
| 2022/0323166 | A1 | 10/2022 | Tilson et al. |

FOREIGN PATENT DOCUMENTS

| | | |
|---|---|---|
| CN | 1706349 A | 12/2005 |
| CN | 1732855 A | 2/2006 |
| CN | 1806770 A | 7/2006 |
| CN | 1861011 A | 11/2006 |
| CN | 101119765 A | 2/2008 |
| CN | 101129255 A | 2/2008 |
| CN | 102137628 A | 7/2011 |
| CN | 201899767 U | 7/2011 |
| CN | 102711585 A | 10/2012 |
| CN | 102872519 A | 1/2013 |
| CN | 103384500 A | 11/2013 |
| CN | 104168860 A | 11/2014 |
| CN | 104287684 B | 3/2016 |
| CN | 105759418 A | 7/2016 |
| CN | 105832279 A | 8/2016 |
| CN | 106137397 A | 11/2016 |
| CN | 106455929 A | 2/2017 |
| CN | 106488744 A | 3/2017 |
| CN | 106659367 A | 5/2017 |
| CN | 107296584 A | 10/2017 |
| DE | 102005039601 A1 | 2/2007 |
| EP | 401129 A1 | 12/1990 |
| EP | 0941743 A2 | 9/1999 |
| EP | 1662972 A2 | 6/2006 |
| EP | 1695657 A1 | 8/2006 |
| EP | 1487318 B1 | 3/2008 |
| EP | 2016914 A2 | 1/2009 |
| EP | 1499227 B1 | 10/2010 |
| EP | 2258322 A2 | 12/2010 |
| EP | 2364637 A1 | 9/2011 |
| EP | 2368481 A1 | 9/2011 |
| EP | 2368483 A1 | 9/2011 |
| EP | 3256052 A1 | 12/2017 |
| GB | 2482355 A | 10/2010 |
| GB | 2497544 A | 6/2013 |
| JP | H05293077 A | 11/1993 |
| JP | 2002125921 A | 5/2002 |
| JP | 2005152300 A | 6/2005 |
| JP | 03965108 B2 | 8/2007 |
| JP | 2009507617 A | 2/2009 |
| JP | 2009061173 A | 3/2009 |
| JP | 2011194126 A | 10/2011 |
| JP | 2013176465 A | 9/2013 |
| JP | 2014124475 A | 7/2014 |
| KR | 10-2015-0131502 A | 11/2015 |
| WO | WO97/43941 A1 | 11/1997 |
| WO | WO99/053827 A1 | 10/1999 |
| WO | WO03/013348 A1 | 2/2003 |
| WO | WO2007/035931 A2 | 3/2007 |
| WO | WO2008/041809 A1 | 4/2008 |
| WO | WO2008/122997 A1 | 10/2008 |
| WO | WO2011/018147 A1 | 2/2011 |
| WO | WO2011/018157 A1 | 2/2011 |
| WO | WO2011/148172 A2 | 12/2011 |
| WO | WO2012/054480 A2 | 4/2012 |
| WO | WO2012/080947 A1 | 6/2012 |
| WO | WO2012/122288 A2 | 9/2012 |
| WO | WO2017/041052 A1 | 3/2017 |
| WO | WO2018/035452 A1 | 8/2017 |
| WO | WO2019/054867 A1 | 3/2019 |
| WO | WO2020/018934 A1 | 1/2020 |
| WO | WO2020/214221 A1 | 10/2020 |
| WO | WO2020/237426 A1 | 12/2020 |
| WO | WO2021/202336 A1 | 10/2021 |
| WO | WO2021/242884 A1 | 12/2021 |
| WO | WO2022/051682 A1 | 3/2022 |
| WO | WO2022/159861 A1 | 7/2022 |
| WO | WO2022/165302 A8 | 8/2022 |
| WO | WO2022/192515 A1 | 9/2022 |

OTHER PUBLICATIONS

Filip et al.; Design, Implementation, and Testing of a miniature self-slabilizing capsule endoscope with wireless image transmission capabilities; Intl. Journal "Information Technologies & Knowledge", 5(1), downloaded from http://www.foibg.com/ijitk/ijitk-vol05/ijitk05-1-p01.pdf on Jul. 28, 2016, (the year of publication is sufficiently earlier than the effective U.S. filing date and any foreign priority date so that the particular month of publication is not in issue) 2011.

Loeve et al.; Endoscope Shaft-Rigidity Control Mechanism: "Forguide"; IEEE Trans. on Biomed. Eng.; 59(2); pp. 542-551; Feb. 2012.

Loeve et al.; Vacuum packed particles as flexible endoscope guides with controllable rigidity; Granular Matter; 12(6); pp. 543-554; Jun. 24, 2010.

Shah et al.; Magnetic Imaging of Colonoscopy: An Audit of Looping, Accuracy and Ancillary maneuvers; Gastrointest. Endosc.; 52(1); pp. 1-8; Jul. 1, 2000.

(56) References Cited

OTHER PUBLICATIONS

Simi et al.; Design, Fabrication, and Testing of a Capsuie With Hybrid Locomotion for Gastrointestinal Tract Exploration; IEEE/ASME Trans on Mechatronics; 15(2); pp. 170-x; Apr. 2010.

Valdastri et al.; Advanced Technologies for Gastrointestinal Endoscopy; Annu. Rev. Biomed. Eng.; 14; pp. 397-429; May 2012.

Zhao et al.; Development of a variable stiffness overtube based on low-melting-point-alloy for endoscopic surgery; J. Med. Devices; 10(2); 8 pages; May 12, 2016.

Tilson et al.; U.S. Appl. No. 17/902,770 entitled "Nested rigidizing devices," filed Sep. 2, 2022.

Tilson et al.; U.S. Appl. No. 17/940,906 entitled "External working channels," filed Sep. 8, 2022.

Dow, Dow white paper: Can you estimate modulus from durometer hardness for silicones: Yes, but you oniy roughly and you must choose your modulus carefuilyl; 5 pages; retrieved from the internet (https://www.dow.com/content/darn/dcc/documents/en-us/tech-art/11/11-37/11-3716-01-durometer-hardness-for-silicones.pdf) on Jan. 18, 2023.

* cited by examiner

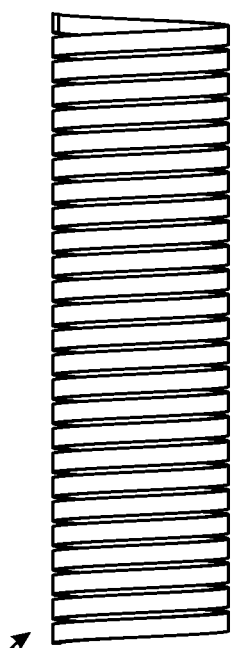
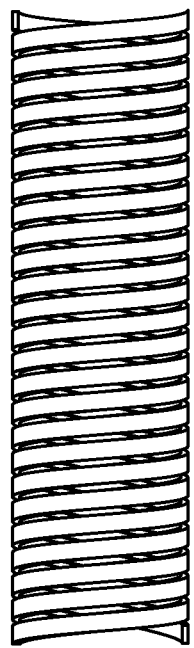
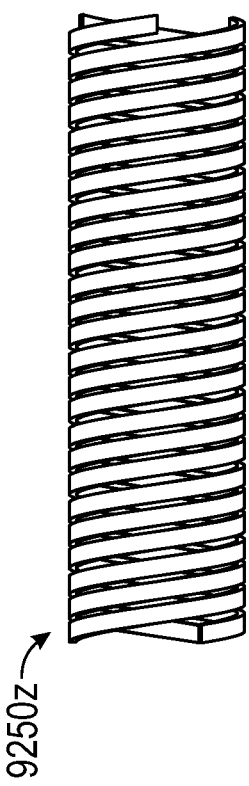
FIG. 10D  FIG. 10E  FIG. 10F
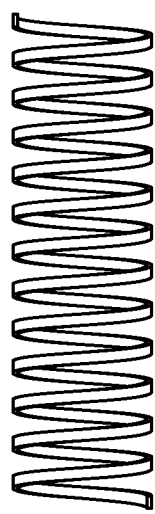
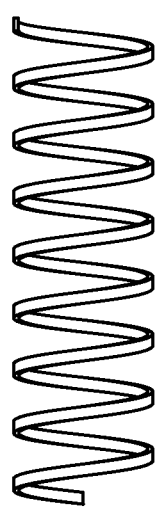
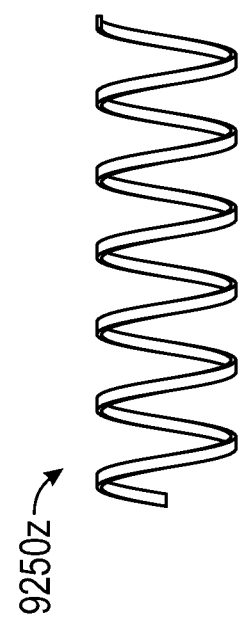
FIG. 10A  FIG. 10B  FIG. 10C

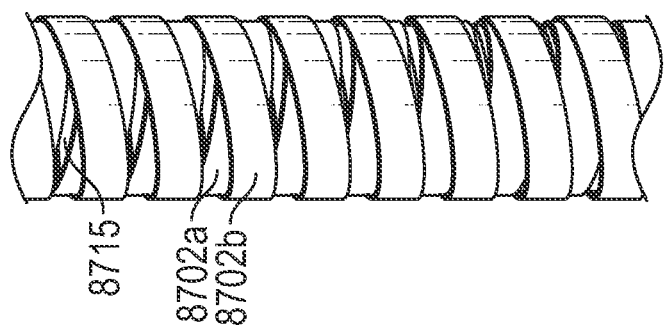
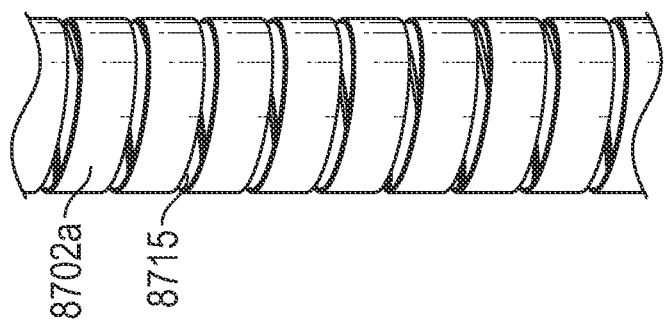
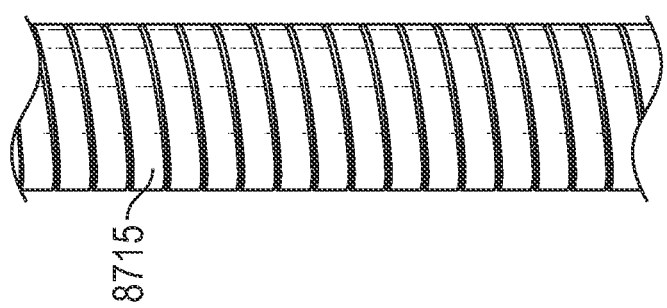
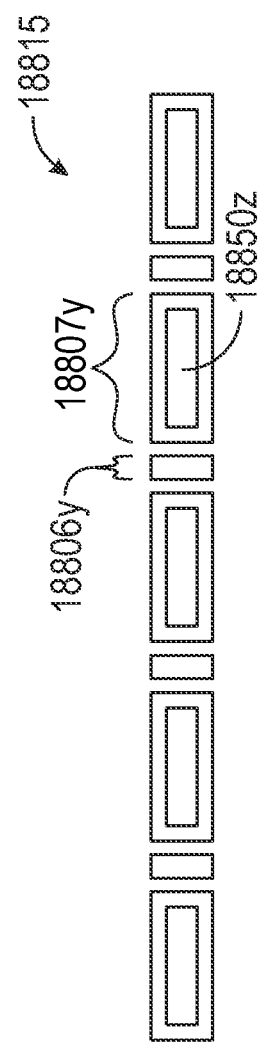

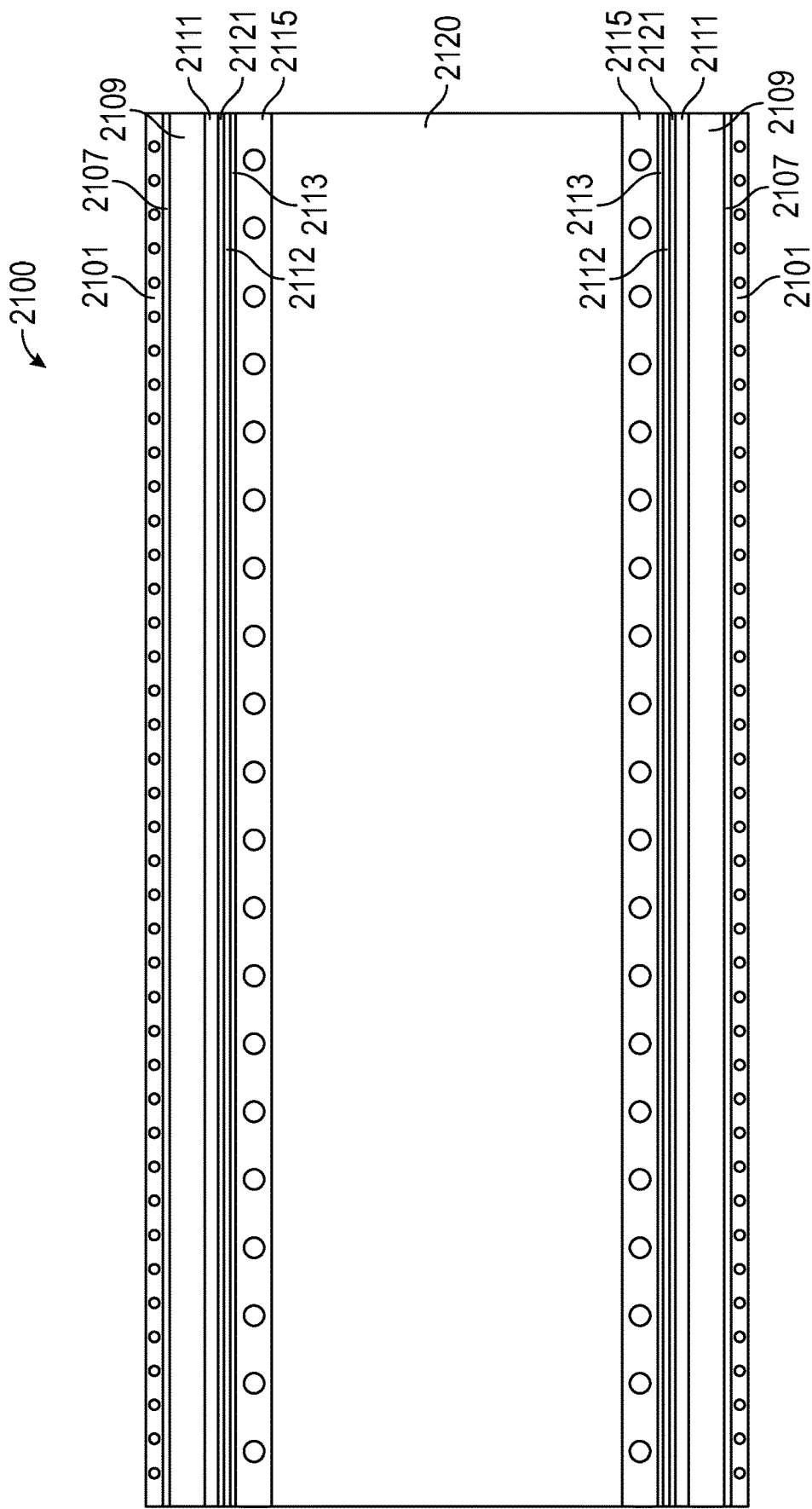

LAYERED WALLS FOR RIGIDIZING DEVICES

CROSS REFERENCE TO RELATED APPLICATIONS

This application is a U.S. National Stage Entry of International Patent Application No. PCT/US2021/024582, filed Mar. 29, 2021, titled "LAYERED WALLS FOR RIGIDIZING DEVICES," which claims priority to U.S. Patent Provisional Application No. 63/002,202, filed on Mar. 30, 2020, titled "COIL WOUND TUBES FOR RIGIDIZING DEVICES," and to U.S. Patent Provisional Application No. 63/030,235, filed on May 26, 2020, titled "LAYERED WALLS FOR RIGIDIZING DEVICES," the entireties of which are incorporated by reference herein.

This application may also be related to International Patent Application No. PCT/US2019/042650, filed on Jul. 19, 2019, titled "DYNAMICALLY RIGIDIZING COMPOSITE MEDICAL STRUCTURES," and published as WO 2020/018934, and/or to International Patent Application No. PCT/US2020/013937, filed on Jan. 16, 2020 and titled "DYNAMICALLY RIGIDIZING COMPOSITE MEDICAL STRUCTURES," the entireties of which are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

During medical procedures, the interventional medical device can curve or loop through the anatomy, making advancement of the medical device difficult.

Gastrointestinal looping, caused when the endoscope can no longer advance due to excessive curving or looping of the gastrointestinal tract, is a particularly well-known clinical challenge for endoscopy. Indeed, one study found that looping occurred in 91 of 100 patients undergoing colonoscopy [Shah et al, "Magnetic Imaging of Colonoscopy: An Audit of Looping, Accuracy and Ancillary maneuvers." *Gastrointest Endosc* 2000; 52: 1-8]. Gastrointestinal looping prolongs the procedure and can cause pain to the patient because it can stretch the vessel wall and the mesentery. Furthermore, gastrointestinal looping leads to an increased incidence of perforations. In severe cases of gastrointestinal looping, complete colonoscopies are impossible since looping stretches the length of the colon and the colonoscope is not long enough to reach the end. Gastrointestinal looping is an impediment to precise tip control, denying the user the coveted one-to-one motion relationship between the handle and the endoscope tip. Such problems commonly occur across a wide range of endoscopic procedures, including colonoscopy, esophagogastroduodenoscopy (EGD), enteroscopy, endoscopic retrograde cholangiopancreatography (ERCP), interventional endoscopy procedures (including ESD (Endoscopic Submucosal Dissection) and EMR (Endoscopic Mucosal Resection)), robotic flexible endoscopy, trans-oral robotic surgery (TORS), altered anatomy cases (including Roux-en-Y), and during NOTES (Natural Orifice Transluminal Endoscopic Surgery) procedures. Accordingly, there is a need for device that helps prevent gastrointestinal looping to provide more successful access to the gastrointestinal tract.

Similar difficulties in advancing medical instruments can arise, for example, during interventional procedures in the lungs, kidneys, brain, cardiac space, and other anatomical locations. Accordingly, there is a need for a device that can provide safe, efficient, and precise access to otherwise difficult to reach anatomical locations.

SUMMARY OF THE DISCLOSURE

In general, in one embodiment, a rigidizing device includes an elongate flexible tube, a stiffening layer positioned radially outwards of the elongate flexible tube, an outer layer over the elongate flexible tube and the stiffening layer, and a vacuum or pressure inlet between the elongate flexible tube and the outer layer and configured to attach to a source of vacuum or pressure. The elongate flexible tube includes a first reinforcement element and a second reinforcement element. The second reinforcement element is counterwound relative to the first reinforcement element. The rigidizing device is configured to have a rigid configuration when vacuum or pressure is applied through the inlet and a flexible configuration when vacuum or pressure is not applied through the inlet.

This and any other embodiments can include one or more of the following features. The stiffening layer can be a braid layer. The rigidizing device can further include a binding layer between the first reinforcement element and the second reinforcement element. The binding layer can include an adhesive. The first and second reinforcement elements can be embedded in a matrix. The binding layer can include a same material as the matrix. The first reinforcement element can be wound at an angle in a positive direction, and the second reinforcement angle can be wound at the same angle in a negative direction. The first reinforcement element or the second reinforcement element can be wound at an angle of greater than 60 degrees and less than 90 degrees relative to a longitudinal axis of the rigidizing device. The first reinforcement element can be positioned radially outwards of the second reinforcement element. The rigidizing device can further include a separating layer between the first reinforcement element and the second reinforcement element. The first and second reinforcement elements can be woven together.

In general, in one embodiment, a rigidizing device includes an elongate flexible tube, a stiffening layer positioned radially outwards of the elongate flexible tube, an outer layer over the elongate flexible tube and the stiffening layer, and a vacuum or pressure inlet between the elongate flexible tube and the outer layer and configured to attach to a source of vacuum or pressure. The elongate flexible tube includes a first sublayer and a second sublayer. The first sublayer includes a first reinforcement element forming a first spiral about a longitudinal axis of the rigidizing device. The second sublayer includes a second reinforcement element forming a second spiral about the longitudinal axis. The second spiral is positioned over spaces between the first spiral. The rigidizing device is configured to have a rigid configuration when vacuum or pressure is applied through the inlet and a flexible configuration when vacuum or pressure is not applied through the inlet.

This and any other embodiments can include one or more of the following features. The stiffening layer can be a braid layer. The rigidizing device can further include a binding layer between the first sublayer and the second sublayer. The binding layer can include an adhesive. The first and second reinforcement elements can be embedded in a matrix. The binding layer can include a same material as the matrix. The first reinforcement element can be wound in a same direction and at a same pitch as the second reinforcement element. The first reinforcement element and the second reinforcement element can be each wound at an angle of greater than 60 degrees and less than 90 degrees relative to a longitudinal axis of the rigidizing device. The second reinforcement element can radially overlap at least a portion of the first reinforcement element. The second reinforcement element can have a width that is 1.5-4 times a width of the spaces between the first spiral. The second reinforcement element can have a width that is smaller than a width of the first reinforcement element.

In general, in one embodiment, a rigidizing device includes an elongate flexible tube, a stiffening layer positioned radially outwards of the elongate flexible tube, an outer layer over the elongate flexible tube and the stiffening layer, and a vacuum or pressure inlet between the elongate flexible tube and the outer layer and configured to attach to a source of vacuum or pressure. The elongate flexible tube includes a reinforcement element spiraled about a longitudinal axis of the device. Neighboring winds of the spiral radially overlap. The rigidizing device is configured to have a rigid configuration when vacuum or pressure is applied through the inlet and a flexible configuration when vacuum or pressure is not applied through the inlet.

This and any other embodiments can include one or more of the following features. The stiffening layer can be a braid layer. The reinforcement element can be tilted at an angle. A width of the reinforcement element can be greater than a pitch of the spiral. The reinforcement element can be embedded in a matrix. The reinforcement element can be wound at an angle of greater than 60 degrees and less than 90 degrees relative to a longitudinal axis of the rigidizing device.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 10A-10F show different coil designs for a layer of a rigidizing device.

FIGS. 15A-15C show torsional layers for a rigidizing device.

FIG. 16 is a cross-section of an exemplary reinforcing layer.

FIGS. 19A-19B show an exemplary pressure rigidizing device.

DETAILED DESCRIPTION (DEVICE)

In general, described herein are rigidizing devices (e.g., overtubes) that are configured to aid in transporting a scope (e.g., endoscope) or other medical instrument through a curved or looped portion of the body (e.g., a vessel). The rigidizing devices can be long, thin, and hollow and can transition quickly from a flexible configuration (i.e., one that is relaxed, limp, or floppy) to a rigid configuration (i.e., one that is stiff and/or holds the shape it is in when it is rigidized). A plurality of layers (e.g., coiled or reinforced layers, slip layers, braided layers, bladder layers and/or sealing sheaths) can together form the wall of the rigidizing devices. The rigidizing devices can transition from the flexible configuration to the rigid configuration, for example, by applying a vacuum or pressure to the wall of the rigidizing device or within the wall of the rigidizing device. With the vacuum or pressure removed, the layers can easily shear or move relative to each other. With the vacuum or pressure applied, the layers can transition to a condition in which they exhibit substantially enhanced ability to resist shear, movement, bending, torque, and buckling, thereby providing system rigidization.

The rigidizing devices described herein can provide rigidization for a variety of medical applications, including catheters, sheaths, scopes (e.g., endoscopes), wires, overtubes, trocars or laparoscopic instruments. The rigidizing devices can function as a separate add-on device or can be integrated into the body of catheters, sheaths, scopes, wires, or laparoscopic instruments. The devices described herein can also provide rigidization for non-medical structures.

Figure 1:
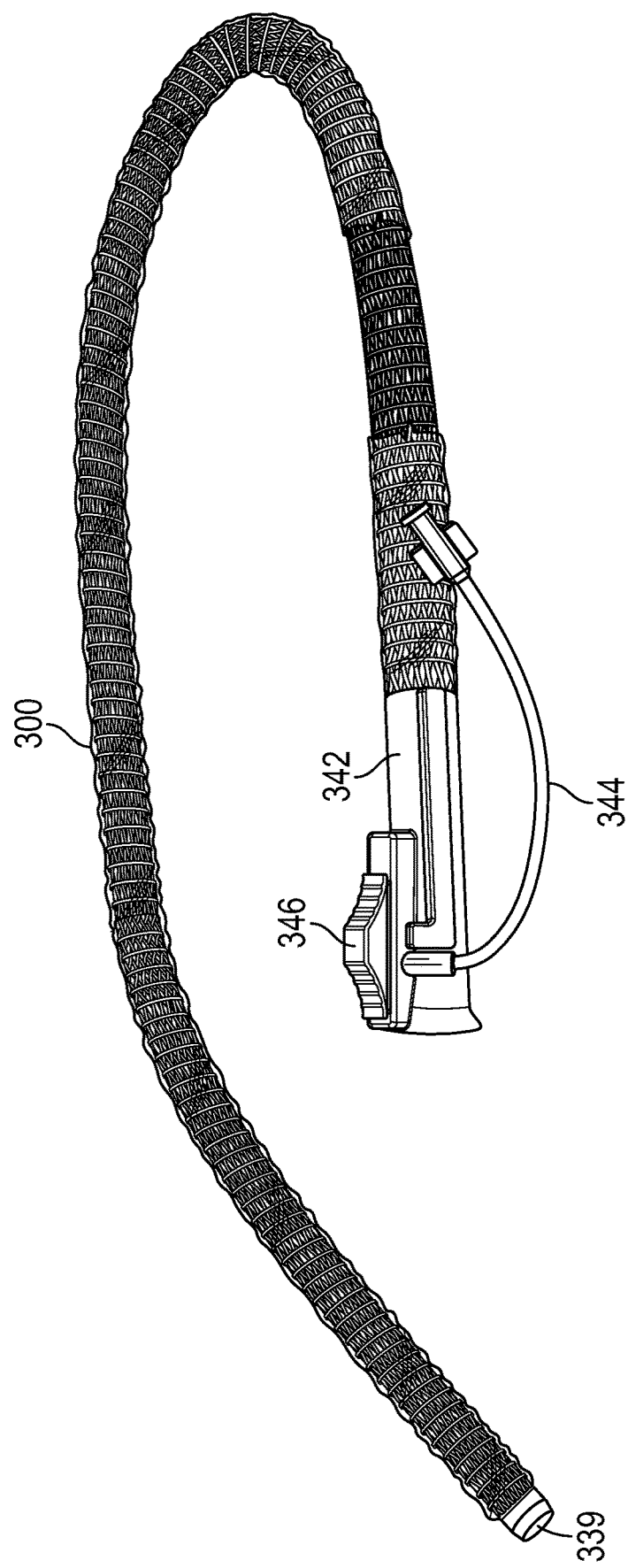
FIG. 1 shows a rigidizing device.

An exemplary rigidizing device system is shown in FIG. 1. The system includes a rigidizing device 300 having a wall with a plurality of layers including a braid layer, an outer layer (part of which is cut away to show the braid thereunder), and an inner layer. The system further includes a handle 342 having a vacuum or pressure inlet 344 to supply vacuum or pressure to the rigidizing device 300. An actuation element 346 can be used to turn the vacuum or pressure on and off to thereby transition the rigidizing device 300 between flexible and rigid configurations. The distal tip 339 of the rigidizing device 300 can be smooth, flexible, and atraumatic to facilitate distal movement of the rigidizing device 300 through the body. Further, the tip 339 can taper from the distal end to the proximal end to further facilitate distal movement of the rigidizing device 300 through the body.

Figure 2:
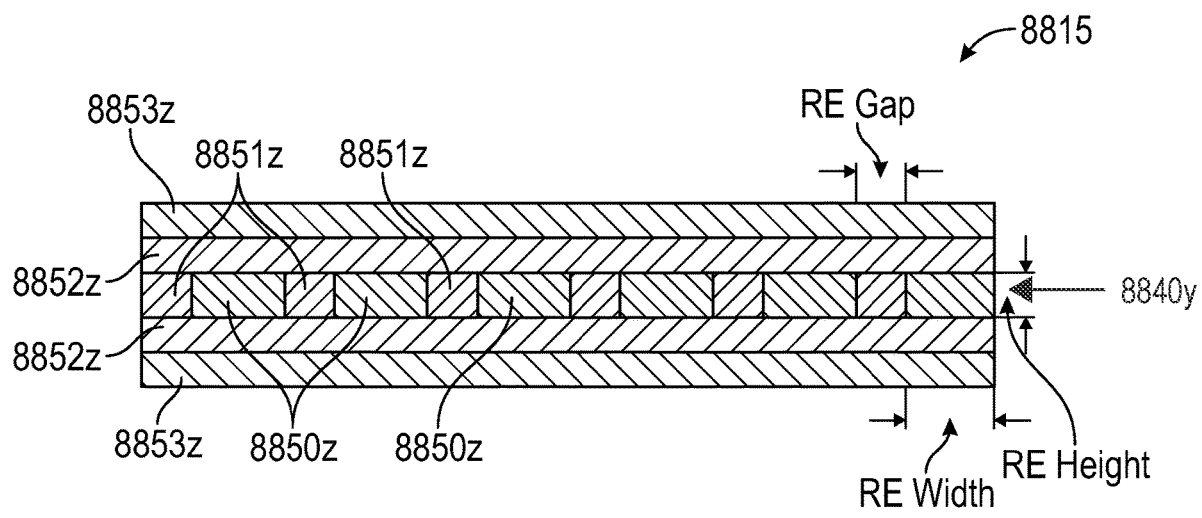
FIG. 2 shows a reinforcing layer of a rigidizing device.

The rigidizing devices described herein can include an innermost layer configured to provide an inner surface against which the additional layers (e.g., braid layer) can be consolidated, for example, when a vacuum or pressure is applied within the walls of the rigidizing device. The layer can further provide a seal for the wall (i.e., can be leak-proof) and can be strong enough to provide resistance to diametrical collapse even during bending of the rigidizing device and/or compression of the rigidizing device during rigidization. Referring to FIG. 2, in some embodiments, the innermost layer 8815 can include a reinforcement sublayer 8840y that includes a reinforcement element 8850z or coil within a matrix 8851z. The reinforcement element 8850z can be a continuous spiral coil or closed rings with gaps therebetween (which may exhibit more resistance to collapse than a spiral coil). If configured as a spiral coil, the reinforcement element 8850z can be spiraled at a constant pitch or at a variable pitch. Additionally, the inner layer 8815 can include an inner film 8852z and an outer film 8853z on one or both sides thereof. In some embodiments, each of the elements 8853z, 8852z, 8850z, 8851z can have a thickness of 0.0002"-0.015", more narrowly 0.0005"-0.001"

The reinforcement element 8850z can be, for example, a metal wire, such as a metal wire made of stainless steel, nitinol, or Tungsten. The reinforcement element 8850z can be, for example, a high strength fiber (e.g., Kevlar, Dyneema, Vectran, Technora, or carbon fiber). The reinforcement element 8850z can be, for example, a stent, a structure cut from a tube, or a braid. In some embodiments, the reinforcement element 8850z can be a round wire (e.g., 0.0005"-0.030" in diameter, such as 0.001", 0.003", 0.005", 0.007" or 0.009" in diameter). In some embodiments, the reinforcement element 8850z can be a rectangular wire (e.g., having a width of 0.001" to 0.100" inch, for instance, 0.010", 0.020", 0.030", 0.040", 0.050", 0.060", 0.070", 0.080", 0.090", or 0.100" and/or a thickness from 0.0003" to 0.020", for instance, 0.001", 0.003", 0.005", 0.007" or 0.010"). In other embodiments, the reinforcement element 8850z can have an oval cross-section and/or can include a plurality of individual strands and/or can have a rectangular cross section in which the four sharp corners are rounded. In some embodiments, the reinforcement element 8850z can be cut from a single tube using, for instance, a laser to create the gaps. In some embodiments, no reinforcement element is used. In some embodiments, the reinforcement element 8850z can be textured (e.g., to improve adhesion and/or shear between neighboring layers). The texturing could be provided, for example, by shot or sand blasting, an abrasive wheel or wipe, or a textured wheel that imprints a pattern.

In some embodiments, the reinforcement element 8850z can be an element with a high aspect ratio (e.g., have a high RE width relative to RE height), such as an aspect ratio of over 5:1, such as over 10:1, such as over 11:1, such as approximately 12:1. Note that in FIG. 2, RE width is the width of reinforcement element 8850z, RE height is height or thickness of reinforcement element 8850z, and RE Gap is distance between reinforcement elements 8850z. The high ratio of width to height of the reinforcement element 8850z can advantageously help prevent external pressure caused parallelogramming-type collapse of the reinforcement elements 8850z within the innermost layer 8815. Parallelogramming-type collapse may occur when the spirals of the coil move from being approximately normal to the axis of the center of the coil towards being parallel to the axis of the center of the coil (the spirals essentially "tip over"). Further, it may be advantageous in preventing parallelogramming if the RE gap between the reinforcement elements 8850z is no more than 3 times the RE height, such as no more than 2 times the RE height, such as no more than 1.5 times the RE height. Additionally, a ratio of the inner diameter of a hollow tube with an innermost layer 8815 to the width of the reinforcement layer 8850z in the innermost layer 8815 of less than 5, such as less than 4.5, such as approximately 4.3, can likewise help prevent parallelogramming-type collapse.

The matrix 8851z may be a very low durometer, for example a TPU or TPE, with a durometer equal to or less than 60 A, 50 A, 40 A, 30 A, 20 A or 10 A. In some embodiments, the matrix 8851z can be TPU, TPE, PET, PEEK, Mylar, urethane, or silicone. Inner and outer films 8852z, 8853z can similarly include TPU, TPE, PET, PEEK, Mylar, urethane, or silicone. In some embodiments, the inner and outer films 8852z, 8853z can be applied by spraying, dipping, wrapping as a sheet or tube, pulling through a bath of solvent, melted, and/or consolidated. In some embodiments, the layer 8815 does not include inner and/or outer films 8852z, 8853z and/or additional films can be included. The inner and/or outer films 8852z, 8853z can create a smooth inner and outer surface.

In a specific example of an innermost layer 8815 for a pressure system, the layer is made at 0.260" inside diameter as a hollow tube with an RE width of 0.050", an RE height of 0.008", and an RE Gap of 0.010". Film 8853z is omitted on both sides. Film 8852z (on both sides of the matrix 8851z and reinforcement elements 8850z) are all made of urethane (600 psi to 100% strain). The thickness of both the matrix 8851z and each film 8852z is about 0.006", giving a total wall thickness of 0.018". This structure can resist collapse at over 10 atm of external pressure.

In a second specific example of an innermost layer 8815 for a pressure system, film 8853z is omitted on both sides. The RE width is 0.050", the RE height is 0.008", and the RE Gap is 0.010". The film 8852z is a higher durometer elastomer, for example an elastomer that has a stress of 2000 psi@ 100% strain and has a thickness of about 0.001" thick. The matrix 8851z can be an 50A urethane. The matrix 8851z can be deposited as thermoplastic elastomer cord stock, for example at 0.008" rectangular cross section or 0.010" round cross section. This cord stock can also be deposited with increased axial modulus (but not transverse modulus) by co-extruding the stock with a wire (for example, 0.001" diameter) or fiber at its core.

In a third specific example of an innermost layer 8815 for a pressure system, the reinforcement element 8850z can be a wire with a high aspect ratio. For example, the layer 8815 can have an RE height of 0.005", an RE width of 0.060" and an RE gap of 0.006" in a rectangular stainless steel wire. The inner diameter of the tube formed with the innermost layer 8815 is 0.26". Elements 8852z and 8851z can be 80 A urethane and can be approximately 0.002" thick. Further, layer 8851z can be a 50 A urethane (e.g., deposited from a heated tank with melted urethane therein and an orifice for precise dispensing via pressure). The structure of this exemplary innermost layer 8815 can resist collapse at over 10 atm of external pressure, such as over 12 atm of pressure, such as over 13 atm of pressure.

In a specific example of an innermost layer 8815 for a vacuum system, the outer film 8853z on one side (e.g., the outer or top side) is omitted, the film 8852z above (outside of) the reinforcement/matrix includes a 0.005" 50 A urethane, the matrix 8851z is made of 0.005" thick 50A urethane, the reinforcement element 8850z is a stainless steel wire, the film 8852z below (inside of) the reinforcement/matrix includes 0.0025" thick 50A urethane, and the bottom outer film 8853z is a 0.004" thick 80A urethane. The RE width is 0.020", the RE height is 0.005", and the RE Gap is 0.010". The bottom outer film 8853z is hydrophilically coated. The inner diameter of the tube formed by layer 8815 is 0.551".

Although shown in FIG. 2 as symmetrical, it should be understood that the innermost layer 8815 need not have a symmetrical arrangement of films 8852z, 8853z. For example, neither layer may be on the bottom (inside of the matrix/reinforcement) while both layers are present on top. Additionally, it should be understood that the material for both innermost films 8852z need not be the same, nor need the material for the both of the outermost films 8853z be the same.

Figure 3:
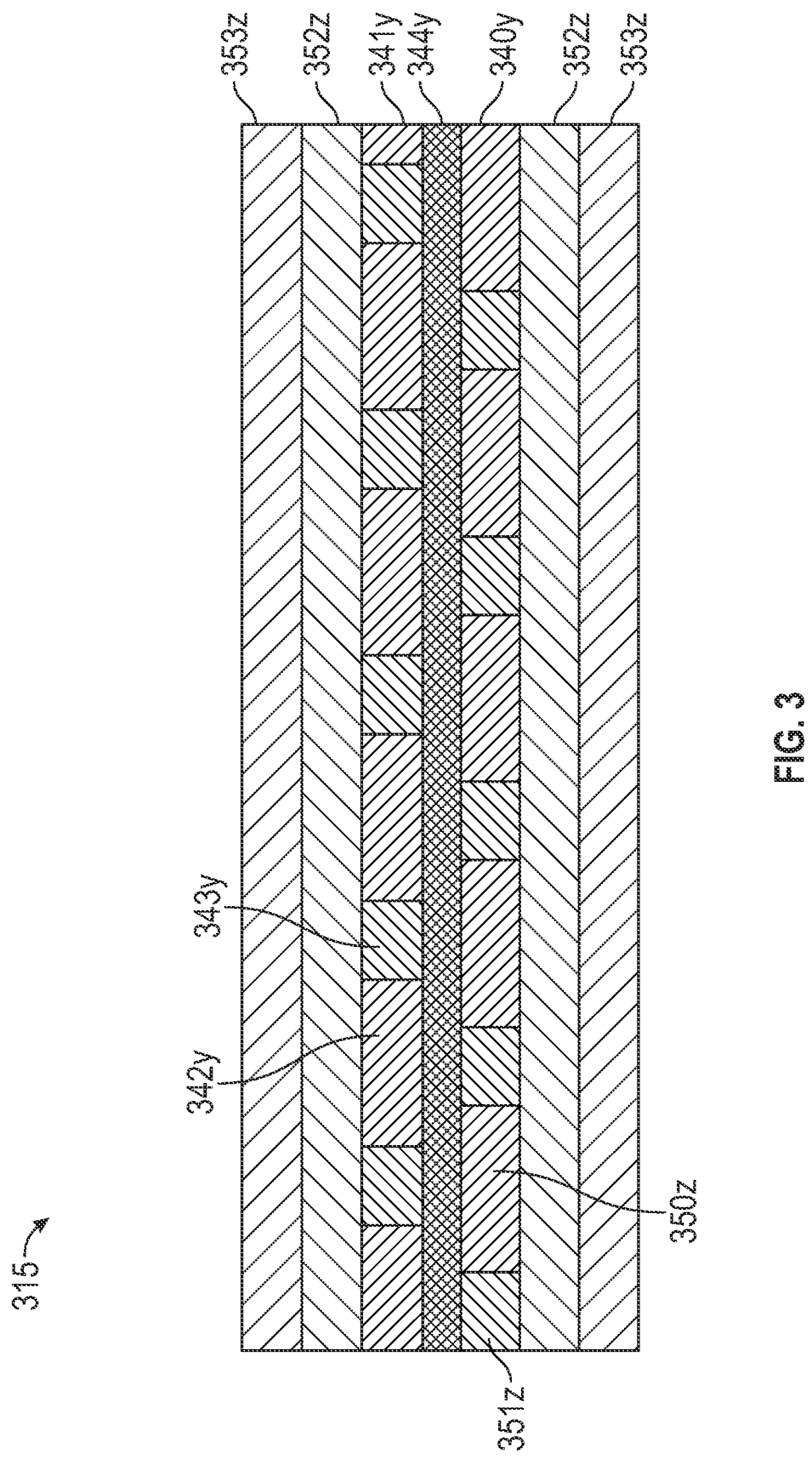
FIG. 3 shows another reinforcing layer of a rigidizing device.

Another exemplary innermost layer 315 is shown in FIG. 3. Layer 315 is similar to layer 8815 except that it includes an additional reinforcement sublayer 341y that includes one or more reinforcement elements 342y within a matrix 343y (i.e., in addition to sublayer 340y with reinforcement elements 350z and matrix 351z). Further, a binding sublayer 344y can be positioned between the reinforcement sublayers 340y, 341y. Similar to innermost layer 8815, the layer 315 can include inner and outer films 352z, 353z, respectively.

The reinforcement sublayer 341y can be identical to or different from the reinforcement sublayer 340y. For example, the reinforcement sublayer 341y can include the same material, size, and shape of reinforcement elements and/or matrices as the reinforcement sublayer 340y or different material, size and shape of reinforcement elements and/or matrices as the reinforcement sublayer 340y. In one specific example, one of the reinforcement sublayers 340y, 341y can include a reinforcement element of 0.005" by 0.030" flat stainless steel wire while the other reinforcement sublayer can include a reinforcement element of 0.002" by 0.020" flat stainless steel wire. In another specific embodiment, the reinforcement element of one of the reinforcement sublayers 340y, 341y can include a round cross-section while the other includes reinforcement elements of flat cross-section (e.g., a flat wire having a width to thickness of between 10:1 and 200:1). As another example, the reinforcement sublayers 340y, 341y can have the same or different thickness.

The binding sublayer 344y can be made, for example, of the same or different matrix material as in matrices 351z, 343y and/or an adhesive and can advantageously prevent the reinforcement elements 350z, 342y from shearing relative to one another during bending of the layer 315, thereby further helping to prevent collapse of the layer 315. In some embodiments, the matrices 351z, 343y and/or binding sublayer 344y can be applied via a bath, dip, or spray as a laminated sheet or as a tube. In some embodiments, the layer 315 may not include the binding sublayer 344y.

In some embodiments, the matrices 351z, 343y and/or binding sublayer 344y can be applied via a bath, dip, spray, or via flat sheet elements that are applied and then co-joined through lamination. In some embodiments, the lamination layer (and/or individual matrices 351z, 343y, or binding sublayer 344y) can be applied as a tube. In some embodiments, the tube can be applied as constructed (for example, as an extrusion). In other embodiments, the tube can be applied and then stretched down over the mandrel with an applied axial load so as to give it both demonstrable change in length (e.g., a length that is 2×, 3×, or 4× the original length) with a resulting commensurate reduction of wall thickness (e.g., a resulting thickness that is ½, ⅓, or ¼ of the original thickness, respectively).

The additional reinforcement sublayer 341y can, in combination with reinforcement sublayer 340y, advantageously help prevent the innermost layer 315 from collapsing (e.g., during the application of pressure to the layer 315). In some embodiments, the additional sublayer 341y may also provide increased torsion resistance.

Figure 4A:
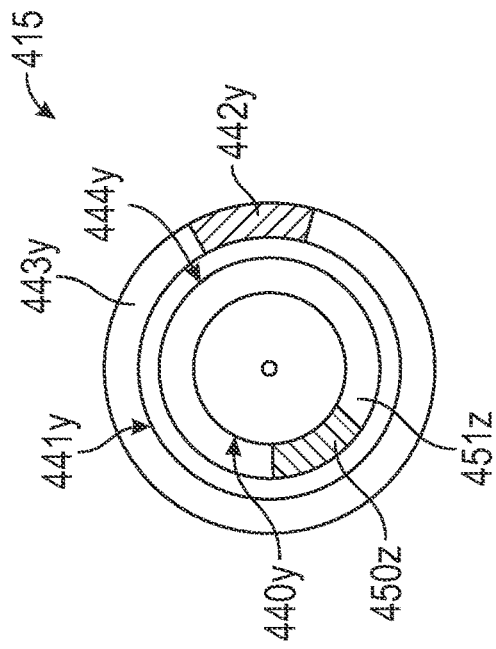
FIGS. 4A-4B show a reinforcing layer having two counterwound reinforcement elements.
Figure 4B:
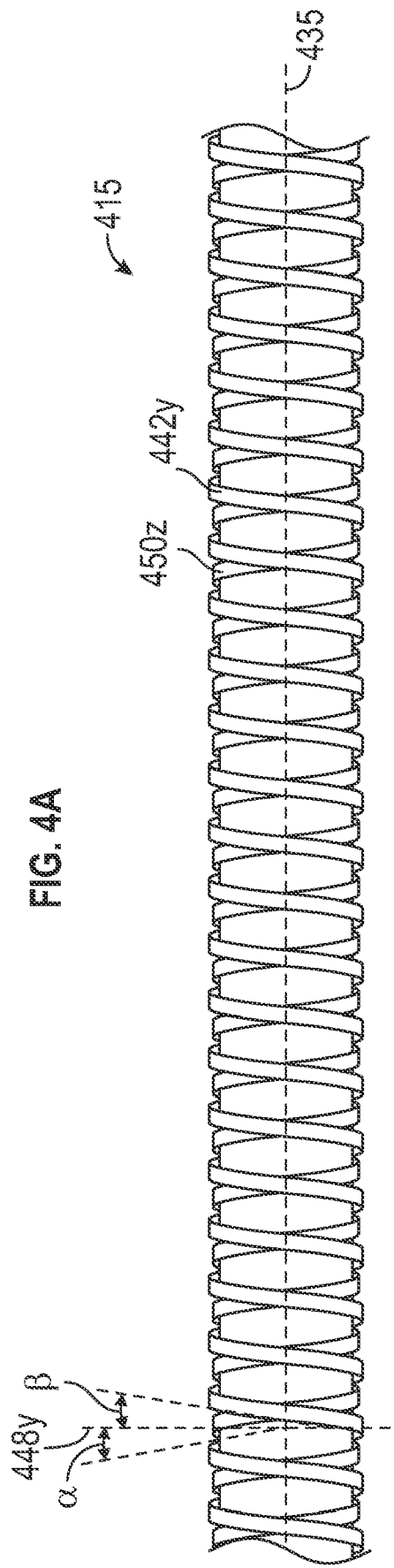

In one embodiment, the reinforcement sublayers (e.g., 340y, 341y) can include reinforcement elements that do not run in parallel to one another. For example, an exemplary inner layer 415 with two reinforcement sublayers layers 440y, 441y separated by a binding sublayer 444y is shown in FIGS. 4A-4B (additional components such as inner and outer films have been removed for clarity). Each reinforcement sublayer 440y, 441y can include one or more reinforcement elements 450z, 442y within a matrix 451z, 443y. In some embodiments, the reinforcement elements 450z and 442y can have substantially the same width. Further, the reinforcement elements 450z, 442y can be counterwound relative to one another. That is, as shown in FIG. 4B, the reinforcement elements 450z of layer 440y can be spiraled around at a negative angle α (e.g., at a negative angle of up to 30 degrees, such as 0.5 degrees to 25 degrees, such as 2 degrees to 15 degrees) relative to an axis 448y that is perpendicular to the longitudinal axis 435 of the rigidizing device. In contrast, the reinforcement elements 442y of reinforcement sublayer 441y can be spiraled around at a positive angle β (e.g., at a positive angle of up to 30 degrees, such as 0.5 degrees to 25 degrees, such as 2 degrees to 15 degrees) relative to the axis 448y. The tendency for the reinforcement element 450z to tip in response to compression may be reduced by winding the reinforcement element 442y at an opposite angle thereover. An exemplary method of manufacturing the layer 415 includes, for example, winding the reinforcement element 450z from left to right, adding binding sublayer 444y, and then winding the reinforcement element 442y from right to left. In some embodiments, the counterwind angle can be modulated, for example, by including multi-start winds, as described below with respect to FIGS. 10A-10F.

In some embodiments, rather than having two separate reinforcement sublayers 440y, 441y, the reinforcement elements 450z, 442y of opposite angle can interleave with one another (i.e., pass above and below one another), such as in a braid. In such an embodiment, the binding sublayer 44y may be omitted.

Figure 5:
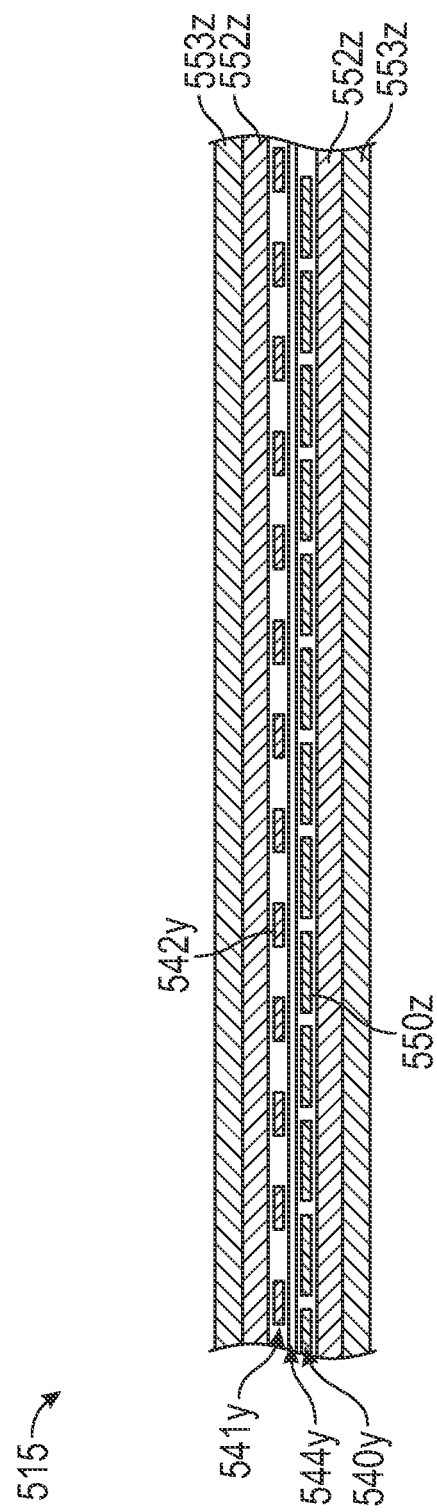
FIG. 5 shows a reinforcing layer having stacked reinforcement elements running parallel to one another.

In some embodiments, the reinforcement sublayers (e.g., 340y, 341y) can include reinforcement element that run in parallel to one another, but overlap across the spacing between reinforcement elements (i.e., across the matrix). For example, an exemplary innermost layer 515 with two reinforcement sublayers 540y, 541y separated by a binding sublayer 544y is shown in FIG. 5. As shown in FIG. 5, the layer 515 can thus include an outer film 553z, an inner film 552z, a sublayer 540y with reinforcement elements 550z (and a matrix that is removed from FIG. 5 for clarity), a binding sublayer 544y, and a sublayer 541y with reinforcement elements 542y (and a matrix that is also removed from FIG. 5 for clarity). The reinforcement elements 542y can run in the same direction and/or at the same angle or pitch as the reinforcement elements 550z. Further, the reinforcement elements 542y of reinforcement sublayer 541y can be positioned over the gaps (or matrix) between the reinforcement elements 550z of reinforcement sublayer 540y. Further, the reinforcement elements 542y can be positioned so as to overlap one or both of the reinforcement elements 550z thereunder. In some embodiments, the outer reinforcement elements 542y can have a width that is 1.5-4 times, such as 2-3 times, the width of the matrix or spacing between reinforcement elements 550z (e.g., so as to still span the entire gap even when the rigidizing device is bent). Having the reinforcement elements 542y overlap the gap or matrix portions between reinforcement elements 550z may advantageously help prevent collapse or penetration of the inner layer 515 at the matrix. Additionally, the second reinforcement sublayer 541y may help prevent the first sublayer 540y from tipping over during pressurization. In some embodiments, the outer reinforcement elements 542y can be thinner or have a smaller width or diameter than the inner reinforcement elements 550z, which can advantageously help maintain the integrity of the inner reinforcement elements 550z when pressurized. In some embodiments, the outer reinforcement elements 542y can be plastic (e.g., PEEK) while the inner reinforcement elements 550z can be metal.

Figure 6:
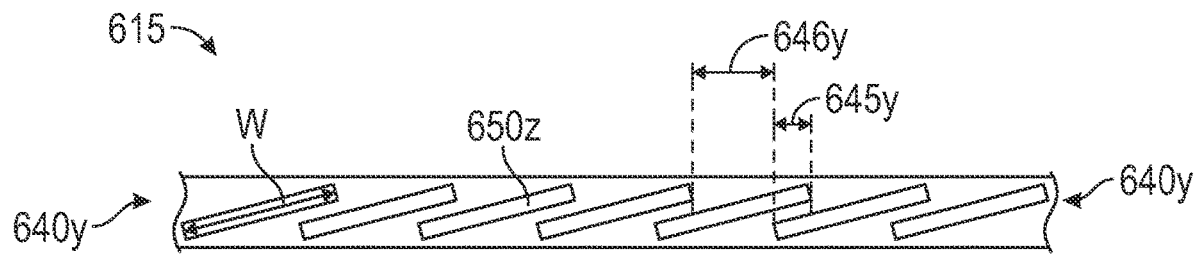
FIG. 6 shows a reinforcing layer having a reinforcement element that is tilted so as to overlap at consecutive winds.

Another exemplary innermost layer 615 is shown in FIG. 6 (layers such as the inner and outer films have been removed for clarity). The innermost layer 615 can include a single reinforcement sublayer 640y including reinforcement elements 650z that are tilted at an angle such that the width w of the reinforcement element 650z is more than the pitch length. Neighboring windings of the reinforcement elements 650z can thus overlap one another (see overlapping zone 645y and non-overlapping zone 646y). For example, the reinforcement element width w can be approximately 0.03", the pitch can be approximately 0.02", and there can be an overlapping zone 645y of approximately 0.003"-0.005". Overlapping reinforcement elements 650z can advantageously help prevent collapse of the layer 615 upon pressurization.

Figure 7:
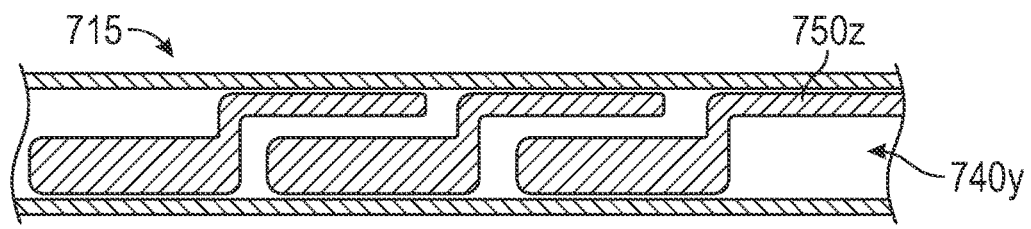
FIG. 7 shows a reinforcing layer having a tiered reinforcement element.

Another exemplary innermost layer 715 is shown in FIG. 7. The reinforcement elements 750z of reinforcement sublayer 740y can have a tiered or stepped cross-sectional structure configured such that the inner portion a first reinforcement element 750z overlaps with the outer stepped or tiered portion of a neighboring reinforcement element 750z. Thus, neighboring reinforcement elements 750z can overlap with one another, which can advantageously help prevent collapse of the layer 715 upon pressurization. The reinforcement elements 750z can be shaped (i.e., have a cross-section) that is tapered, straight, rounded, or wavy.

Figure 14:
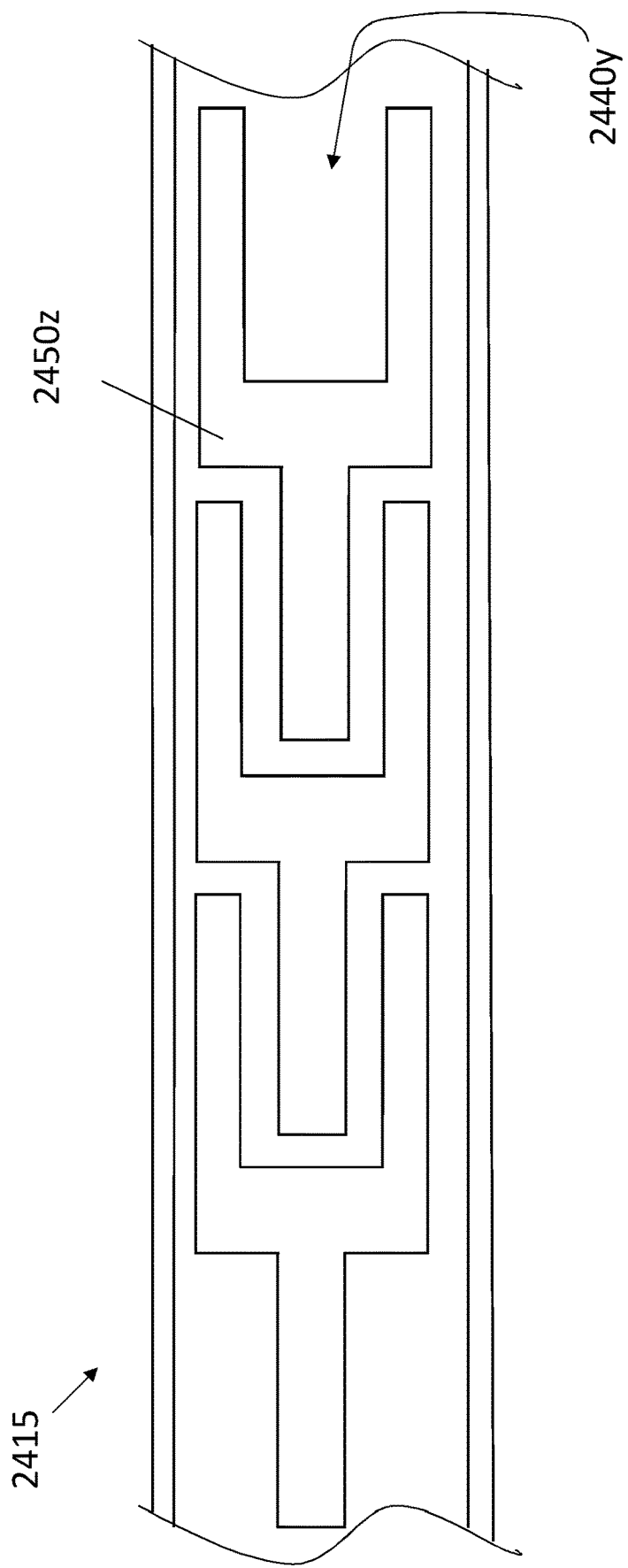
FIG. 14 shows a reinforcing layer element having overlapping reinforcement elements.

Another exemplary innermost layer 2415 is shown in FIG. 14. The reinforcement elements 2450z of reinforcement sublayer 2440y can have a cross-sectional shape similar to a tuning fork with two (outer and inner) laterally/axially extending features. Neighboring reinforcement elements 2450z can fit between the laterally/axially extending features to overlap. Again, the overlapping reinforcement elements 2450z can advantageously help prevent collapse of the layer 2415 upon pressurization.

Figure 8:
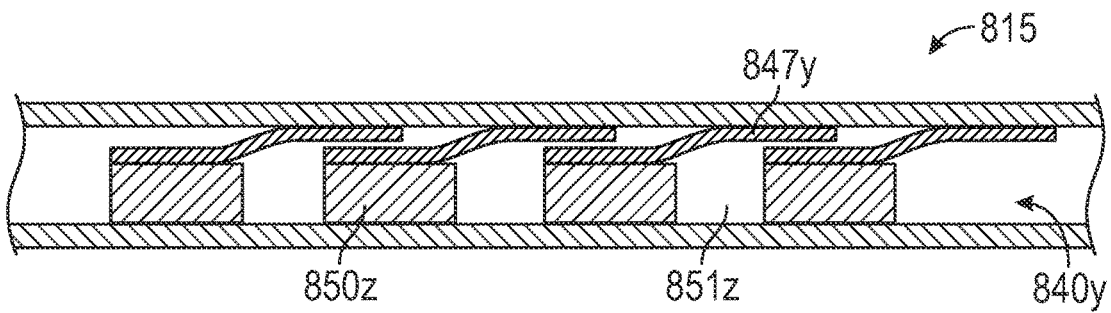
FIG. 8 shows a reinforcing layer having a reinforcement element with an axially extending cover.

Another exemplary innermost layer 815 is shown in FIG. 8. The reinforcement elements 850z of layer 840y can include a covering 847y extending axially therefrom so as to cover the matrix 851z between the reinforcement elements 850z. The covering 847y can have a thickness (e.g., in the radial direction) that is smaller than the thickness of the reinforcement elements 850z (e.g., the thickness of the covering 847y can be less than 50%, less than 40%, less than 30%, or less than 20% of the thickness of the reinforcement elements 850z). Further, as shown in FIG. 8, the covering 847y can be layered over and/or overlap with the outer surface of the reinforcement element 850z. In some embodiments, the covering 847y may be, for example, a thin metal or plastic that is joined to the reinforcement elements 850z.

Figure 9:
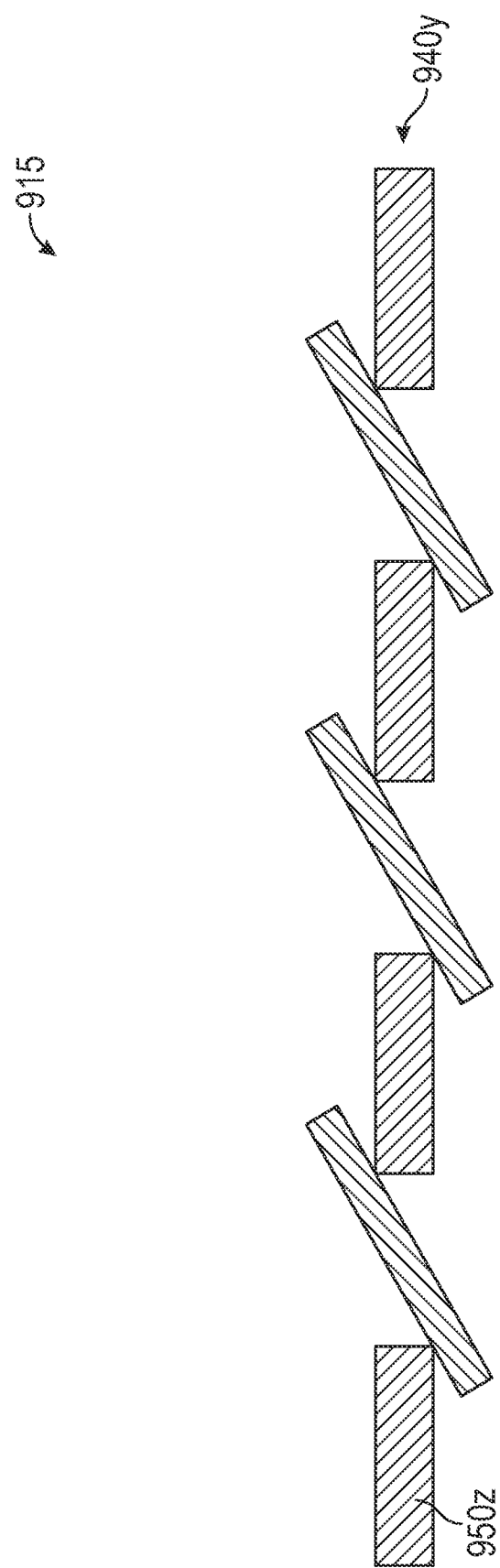
FIG. 9 shows a reinforcing layer having alternating flat and tilted winds of a reinforcement element.

Another exemplary innermost layer 915 is shown in FIG. 9. The reinforcement elements 950z of layer 940y can be arranged such that neighboring reinforcement elements 950z overlap one another. For example, one reinforcement element 950z can be flat (i.e., flattened along the circumference of the rigidizing device) while the adjacent reinforcement element 950z can be angled (i.e., relative to the circumference of the rigidizing device). The angled reinforcement element 950z can extend from underneath a first flat reinforcement element 950z to over the top of a second flat reinforcement element 950z. Neighboring reinforcement elements 950z can be spiraled at substantially the same pitch. In some embodiment, neighboring reinforcement elements 950z can be connected together (e.g., adhered, welded, or otherwise joined).

Multiple sublayers and/or overlapping reinforcement elements as described herein can be used for increased pressure resistance and/or torsion resistance.

The reinforcement elements of the innermost layer can be in a variety of additional configurations. As shown in FIGS. 10D-10F, the reinforcement element 9205z can be a multistart coil winding (e.g., 2 starts as shown in FIG. 10F, three starts as shown in FIG. 10E, or four starts as shown in FIG. 10D). When multi-start coil windings are used the gap between reinforcement elements along the longitudinal axis can be the same as with a single coil, but number of starts can be 2, 3, 4, 5, 6, 7, 8, 9 or even more. While a single start creates a wire angle that is nearly vertical (for example, 2 degrees off of vertical), a multi-start approach creates a wire angle that biases the coils to tilt in one direction, much further away from vertical (for example, 4, 6, 10, 15, or even 20 degrees). This larger angle may serve to make the innermost layer less likely to tilt or structurally collapse under pressure, as the coils with the larger pitch tend to brace against one another for stability. FIGS. 10A-10C show individual starts (coils) from the multistart reinforcement elements 9205Z. FIG. 10C shows one coil from FIG. 10F, FIG. 10B shows one coil from FIG. 10E and FIG. 10A shows one coil from FIG. 10D. In some embodiments, multi-starts can be used in multiple reinforcement sublayers so as to provide overlapping reinforcement elements. Multistart count can be modulated to adjust the reinforcement angle relative to the center axis of the device. Further, multi-start elements can be solid single filaments or multifilament elements such as strands and cable.

Any of the spiraled or coiled reinforcement elements described herein can be replaced or combined with other reinforcement elements, such as laser-cut tube, discrete wire segments, injection molded elements, case elements, links with pivots, or links with flexures.

Figures 11A, 11B:
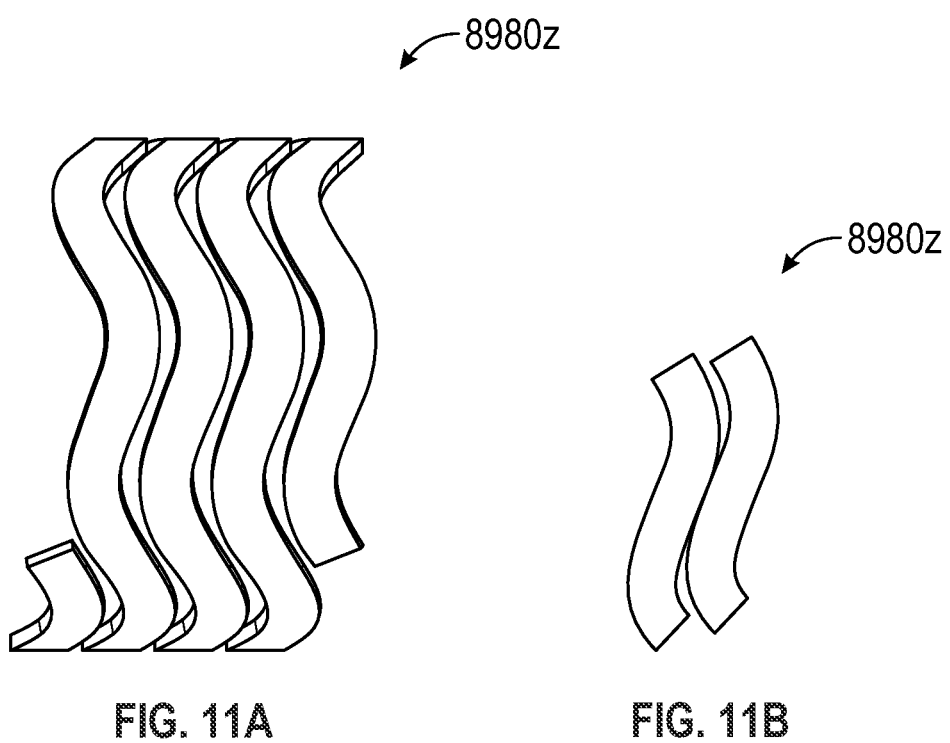
FIGS. 11A-11B show undulating reinforcement elements for a layer of a rigidizing device.

For example, in some embodiments, referring to FIGS. 11A-11B, the reinforcement elements 8950z can be a series of wavy or undulated wires (or an undulated wire that is coiled as described herein). As shown in FIG. 11B, when the device is loaded, the undulated reinforcement elements 8950z moves toward colliding with itself, compressing the matrix 8851Z in between the wires and resisting a parallelogram-type collapse. In one specific embodiment, an innermost layer with such an undulating wire can have an RE height of 0.005", an RE width of 0.060" and an RE gap of just 0.006". The undulating wave can vary +/−0.03" from a centerline (that is, have a wave amplitude of 0.060"). The wave can repeat every 0.3" (that is, have a wavelength of 0.3").

Figure 12A:
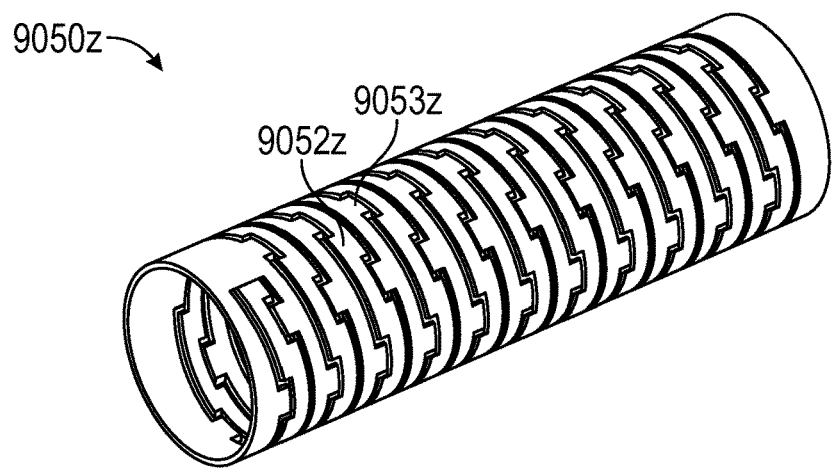
FIGS. 12A-12E show notch and pocket reinforcement elements for a layer of a rigidizing device.
Figure 12B:
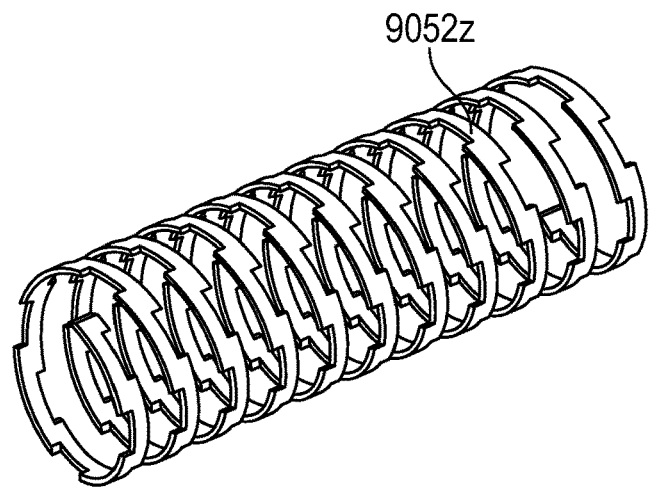
Figure 12C:
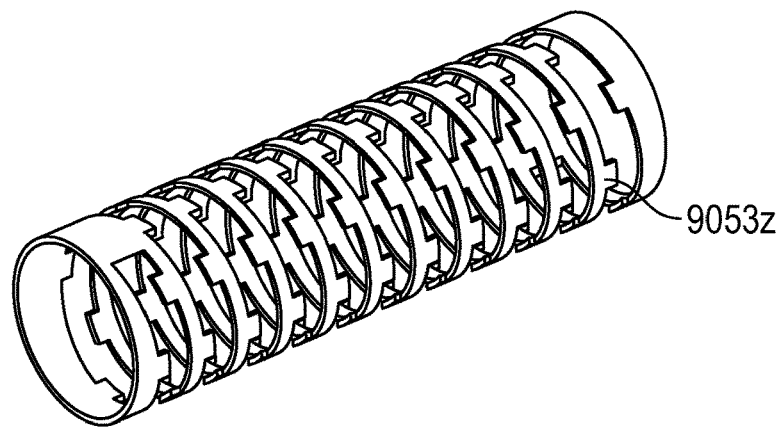
Figure 12D:
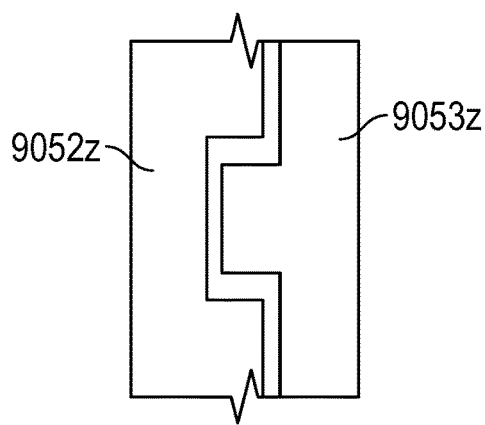
Figure 12E:
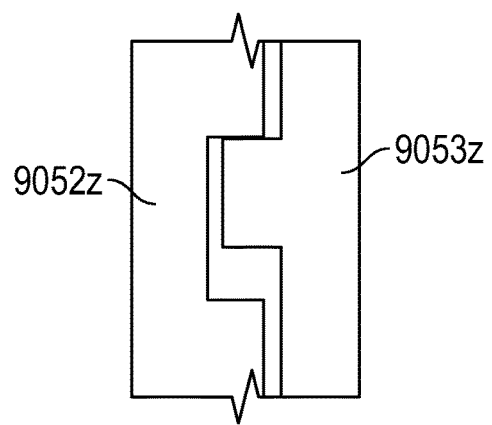

In some embodiments, referring to FIGS. 12A-12C, the reinforcement elements 9050z can include alternating pocket wires 9052z and notched wires 9053z. When unloaded, the pockets and notches of each respective element can be separate (as shown in FIG. 12D). However, when loaded, the notch of wire 9053z moves toward colliding with the pocket of wire 9052z (as shown in FIG. 12E) compressing the matrix 8851z in between the wires and resisting a parallelogram-type collapse.

Figure 13A:
FIGS. 13A-13C show a cut tubing reinforcement element for a layer of a rigidizing device.
Figure 13B:
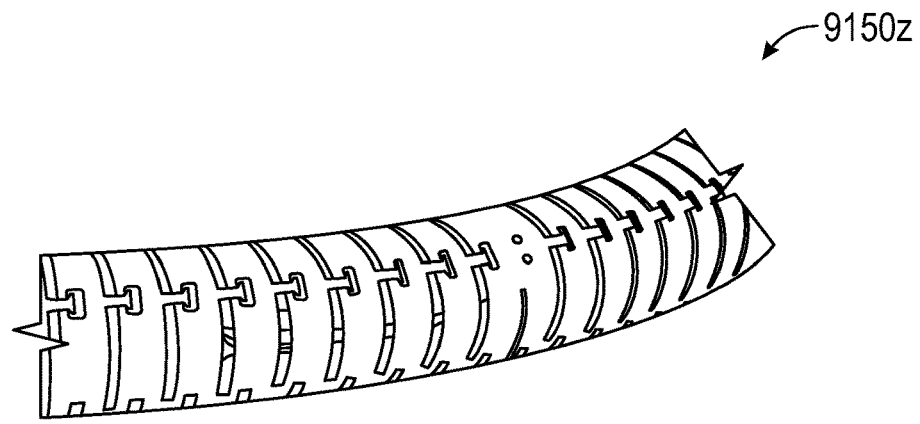
Figure 13C:
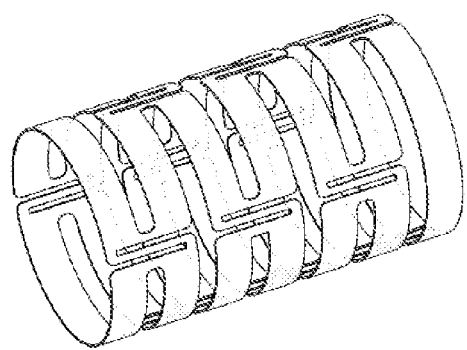

In some embodiments, referring to FIGS. 13A-13C the reinforcing elements 9150z can be a flexure design, e.g., laser cut from a metal or plastic tube. In some embodiments, the flexure design can be configured to bend and/or expand and contract radially while resisting foreshortening. FIG. 13C shows an exemplary flexure design for a reinforcing element 9150z that allows radial expansion (e.g., for ease of assembly and manufacturability) and also provides a radial hard stop under pressure (e.g., to prevent collapse).

In some instances, the reinforcement element can be separate from the inner layer. For instance, the reinforcement element can be positioned diametrically inside or outside the inner layer. The innermost layer can have a hardness, for example, of 30A to 80A. Further, the innermost layer can have a wall thickness of between 0.0005" and 0.060". In some embodiments, the innermost layer can include lubrication or a coating (e.g., hydrophilic coating) on the inner surface thereof to improve sliding of an endoscope or other instrument therethrough. The coating can be hydrophilic (e.g., a Hydromer® coating or a Surmodics® coating) or hydrophobic (e.g., a fluoropolymer). The coating can be applied, for example, by dipping, painting, or spraying the coating thereon. The innermost layer can be a laminated layer with a low frictional coefficient.

For any of the reinforced layers described herein (e.g., innermost layer 8815), the matrix surrounding the reinforcement element can be comprised of a material with high hydrolytic stability. That is, it is advantageous for the rigidizing devices described herein to maintain their structural integrity when exposed to an immersive fluid environment, such as water, saline, gastric fluids, or blood. If the matrix material is hygroscopic and thus absorbs fluid, the fluid may act as a plasticizer and soften the matrix, which can result in a reduction in resistance to pressurized (or vacuum-based) structural collapse and therefore a reduction in the rigidization of the device. As such, in some embodiments, the matrix can be made of a hydrophobic material, thereby absorbing little to no fluid and advantageously maintaining its structural integrity even when immersed in fluid. For example, the matrix can be made of polyethylene, polypropylene, polystyrene, thermoplastic elastomers (such as Chronoprene™ and Teknor Apex Medalist™), or polyvinyl chloride. As another example, the matrix can be made of a compounded solution, such as styrene-ethylene-butylene-styrene (SEBS), styrene-butadiene-styrene copolymer (SBS), or a styrenic block copolymer (SBC), such as Kraton®, that includes polystyrene blocks and rubber blocks, e.g., rubber blocks of polybutadiene or polyisoprene. In some embodiments, the matrix material can include an additive to enhance bonding, such as maleic anhydride.

For any of the reinforced layers described herein (e.g., innermost layer 8815), the reinforcement element and the matrix can be bonded together with an adhesive. For example, the reinforcement element can have the adhesive dipped, sprayed, or immersively applied thereto, and then the reinforcement element can be positioned within the matrix so as to co-join the matrix and the reinforcement element. In some embodiments, the reinforcement element and matrix can have a resulting bond strength of up to 50 pounds per square inch. The adhesive can be, for example, Chemlok™ adhesive. By using an adhesive to adhere the reinforcement elements to the matrix, the reinforced layer can remain intact to resist pressure and/or vacuum collapse.

For any of the reinforced layers described herein (e.g., innermost layer 8815), the reinforced layer can be manufactured such that the layer has a final diameter (i.e., within the rigidizing device) that is at or near its net (i.e., manufactured) diameter, thereby ensuring that the matrix is not required to hold the reinforcement element to a specific diameter. For example, the final diameter of the reinforced layer can be within 10% of the net diameter, such as within 5%, such as within 2% of the net diameter. Having a final diameter near the net diameter can advantageously ensure that the internal stresses of the reinforced layer are reduced, thereby reducing creep and/or failure of the reinforced layer. In some embodiments, the reinforcement element can be manufactured, for example, by yielding the reinforcement element as it is being applied to the matrix, such as by running the reinforcement element through a series of deformation rollers.

Any of the layers described herein may include multiple reinforcement sublayers (e.g., similar to sublayers 340y, 341y) layered adjacent thereto. For example, the innermost layer can include sublayers thereover (e.g., instead of embedded therein). The sublayers can include, for example, one or more ribbons or wires that are spiraled around at an angle (e.g., at an angle of less than 90 degrees, such as greater than 60 degrees and less than 90 degrees, such as 65 degrees to 89.5 degrees, such as 75 degrees to 88 degrees relative to the longitudinal axis of the rigidizing device). For example, as shown in FIGS. 15A-15C, the innermost layer 8715 can have a first sublayer 8702a thereover that is wrapped in a first direction and a second sublayer 8702b thereover that is wrapped in a second opposite direction (e.g., the first sublayer 8702a can be wrapped at 70 degrees, and the second sublayer 8702b can be wrapped at −70 degrees with respect to the longitudinal or horizontal axis). Adding layers 8702a and 8702b may increase the torsion resistance of a finished device. In some embodiments (e.g., in embodiments where increased flexibility is desired), the two sublayers 8702a, 8702b can shear or slide relative to one another. For example, there can be a slip layer between the two layers 8702a, 8702b. In some embodiments, there can be a slip layer between the two sublayers and/or between the other layers of the device (e.g., the innermost layer). In some embodiments, the additional sublayers 8702a, 8702b can be part of or interwoven with another layer (e.g., a braid layer). In embodiments where increased torsion stiffness is desired, the sublayers can be made of a material that can withstand both high tensile and high compressive loads (such as sheet metal or wire) or a material that can withstand a high tensile load but only a small compressive load (such as a plurality of small diameter wires or fibers).

Any of the reinforced layers described herein (e.g., innermost layer 8815) can be configured to include alternating types of material along the longitudinal axis of the device. For example, referring to FIG. 16, the layer 18815 can include alternating sections 18807y and 18806y of high durometer material and low durometer material, respectively. Further, the section 18807z of high durometer material can include the reinforcement element 18850z embedded therein. In some embodiments, the alternating sections 18807y and 18806y can be formed by spiraling section 18807y, but leaving gaps between the spirals that are subsequently filled with the lower durometer material of section 18806y. This design can advantageously enable the layer 18815 to have high stiffness at sections 18807y while enabling flexibility and bending at hinge points created by sections 1880*y*. Accordingly, the device incorporating layer 18815 can have a high stiffness and resistance to pressure/vacuum collapse while still maintaining high baseline flexibility.

Figure 21A:
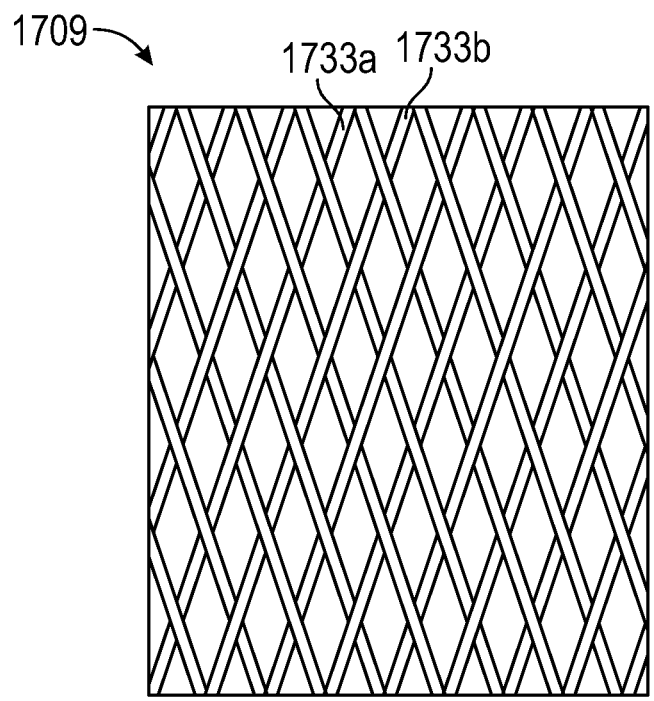
FIGS. 21A-21E show exemplary braid formations.
Figure 21B:
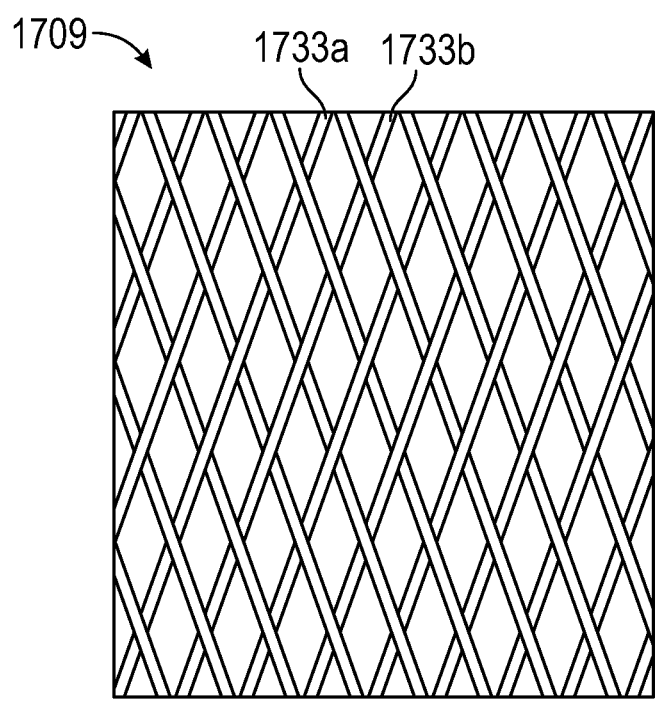
Figure 21C:
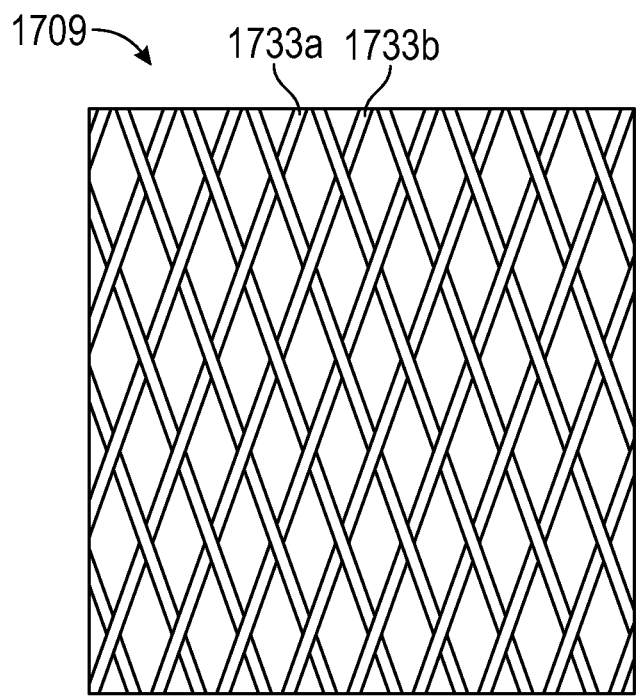
Figure 21D:
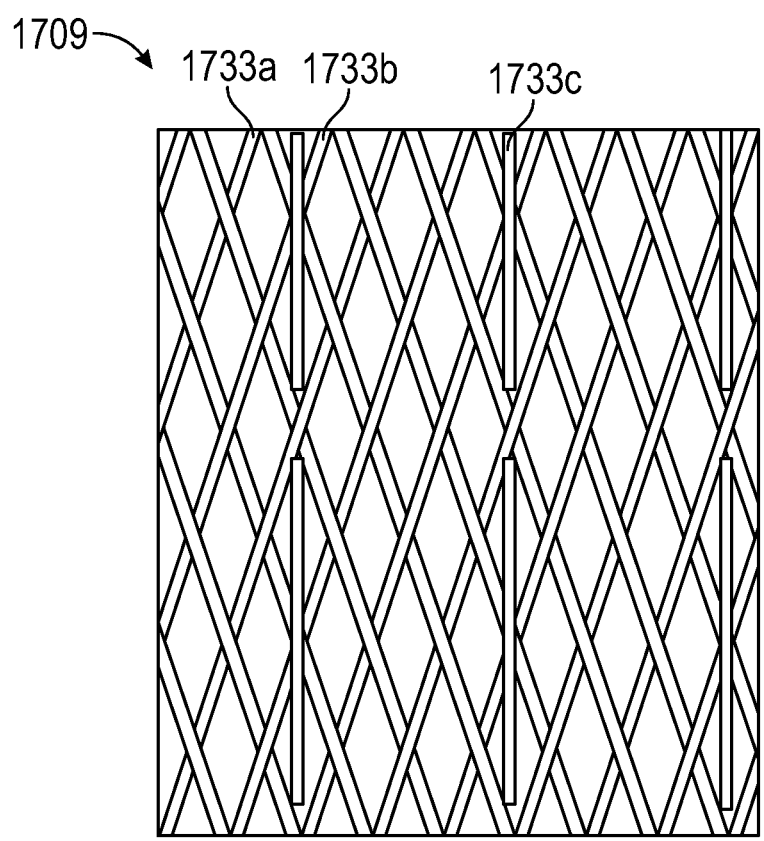
Figure 21E:
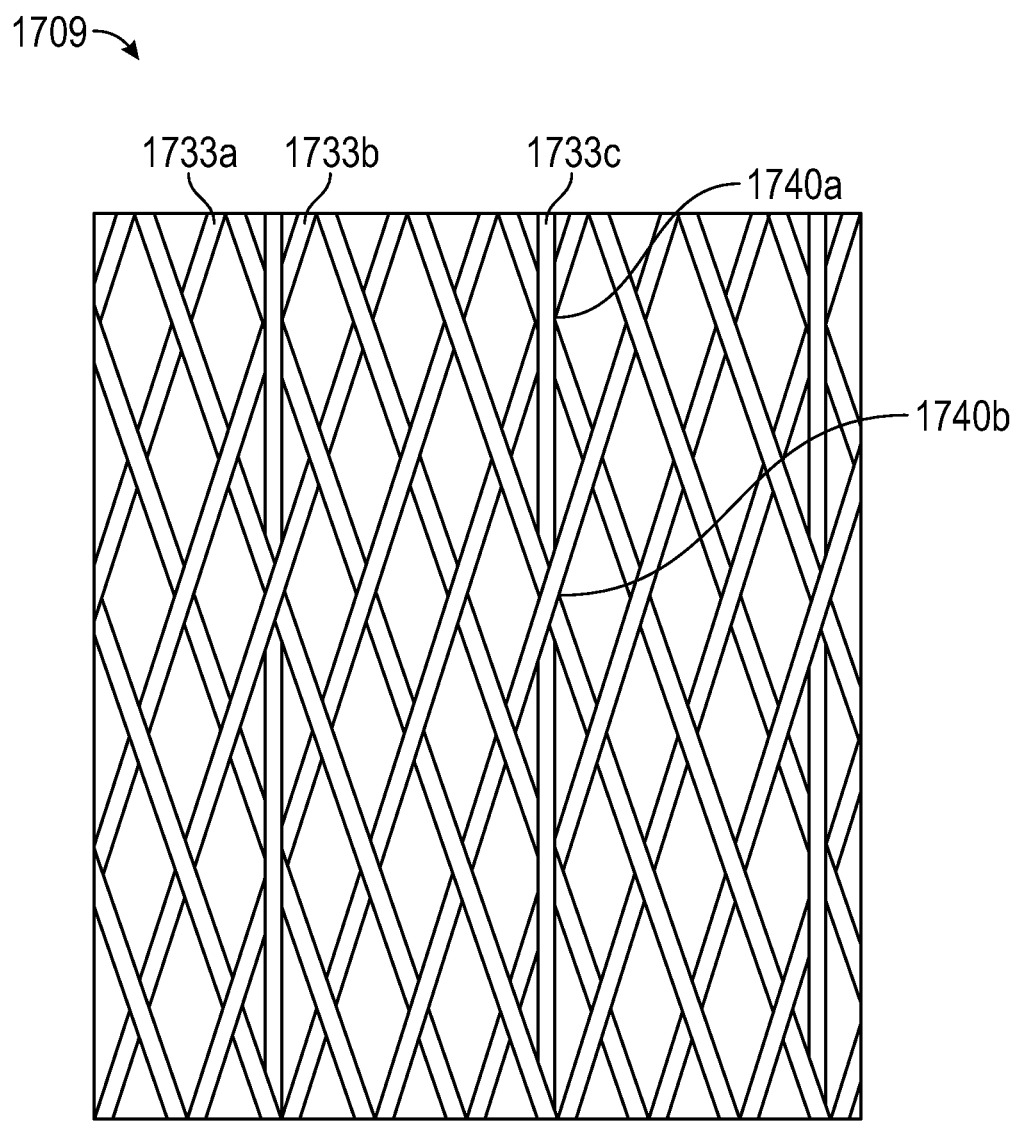

Referring to FIGS. 21A-21E, the braid of any of the rigidizing devices described herein can be in a variety of different braid patterns. For example, referring to FIG. 21A, the braid of layer 1709 can be a diamond full load pattern in which two neighboring strands 1733*a,b* extend over two strands and then under two strands. Referring to FIG. 21B, the braid of layer 1709 can be a full load pattern, in which each strand 1733*a* extends over two strands and under two strands in a manner that is opposite to the neighboring strand 1733*b*. Referring to FIG. 21C, the braid of layer 1709 can be a diamond half load pattern in which each strand 1733*a* extends over one strand and under one strand opposite to the neighboring strand 1733*b*. Referring to FIGS. 21D and 21E, the braid of layer 1709 can include one or more longitudinal strands 1733*c* running through the crossed strands 1733*a*, 1733*b*. The longitudinal strands 1733*c* can be discontinuous (as shown in FIG. 21D) or continuous (as shown in FIG. 21E). Further, in some embodiments and as shown in FIG. 21E, the longitudinal strands 1733*c* can pass over a first strand junction 1740*a* of the braided strands 1733*a*, 1733*b* and under a second junction 1740*b* of the braided strands 1733*a*, 1733*b*. In some embodiments, the over and under junctions 1740*a*, 1740*b* can be adjacent to one other. In other embodiments, the over and under junctions 1740*a*, 1740*b* can be 2-50, such as 2, 3, 4, 10, 20, or 40 junctions away from one another.

The strands of any of the braid layers described herein can be rectangular/flat (e.g., with a long edge of 0.001"-0.060", such as 0.005", 0.007", 0.010", or 0.012", and a short edge of 0.0003"-0.030", such as 0.001", 0.002", or 0.003"), round (e.g., with a diameter of 0.001"-0.020", such as 0.005", 0.01", or 0.012"), or oval. In some embodiments, some of the strands can be flat and some of the strands 233 can be round.

Figure 22A:
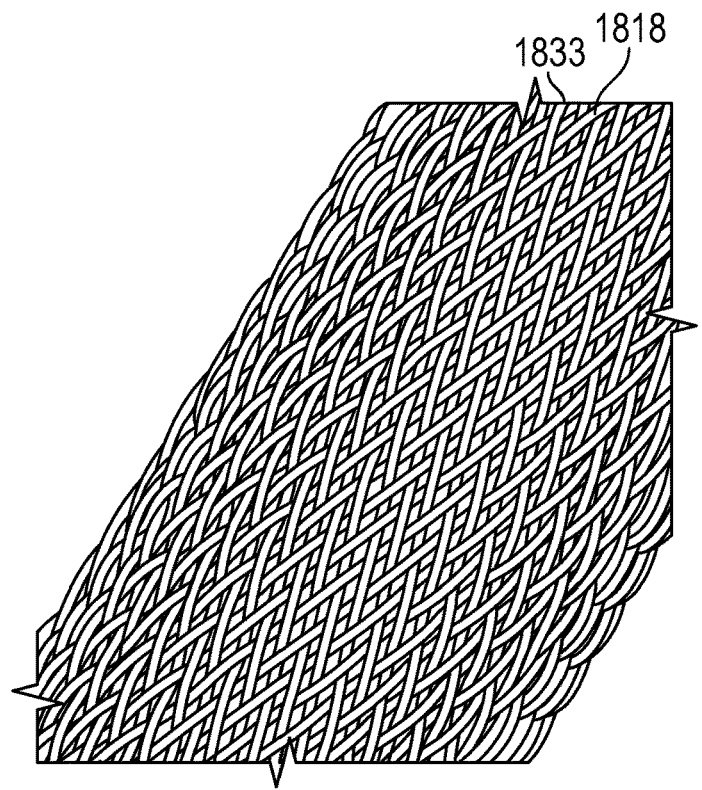
FIGS. 22A-22B show exemplary braid formations.
Figure 22B:
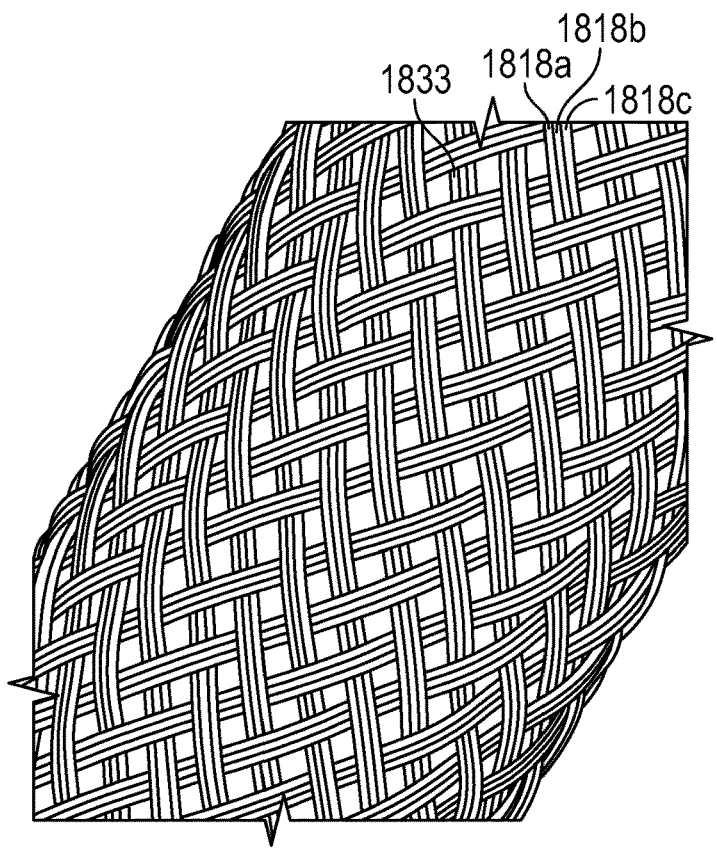
Figure 23A:
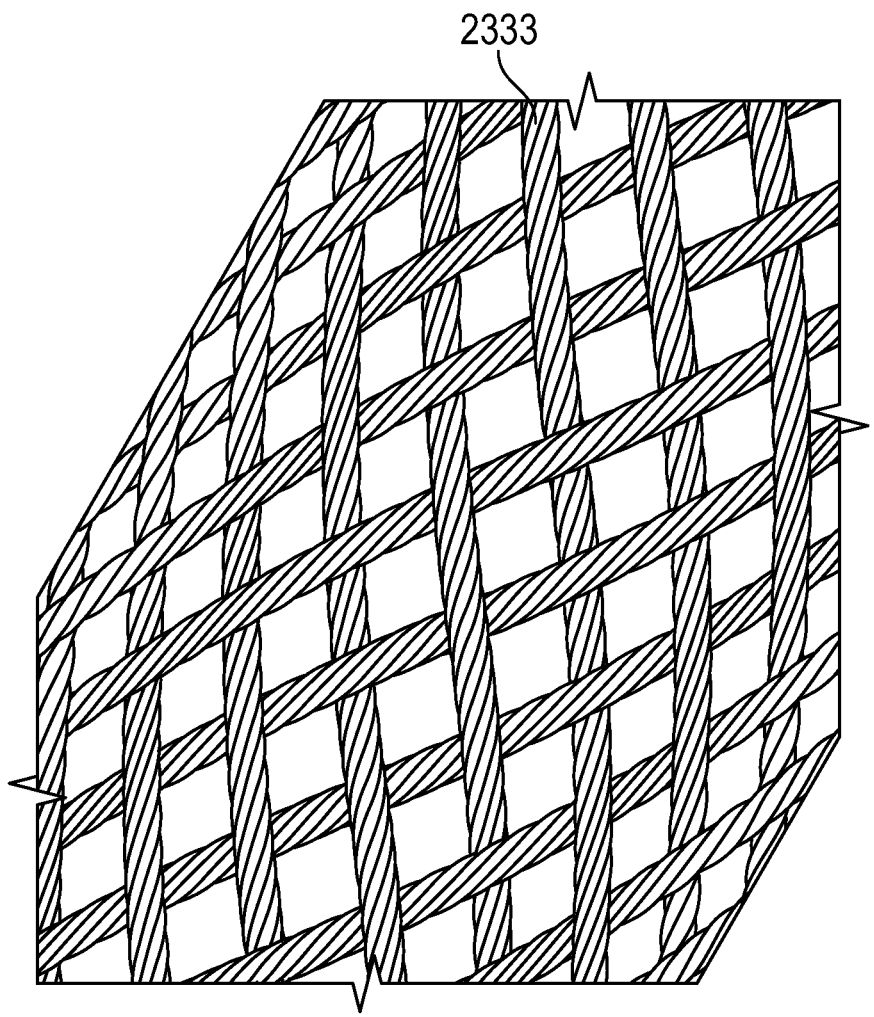
FIGS. 23A-23C show exemplary braid formations.
Figure 23B:
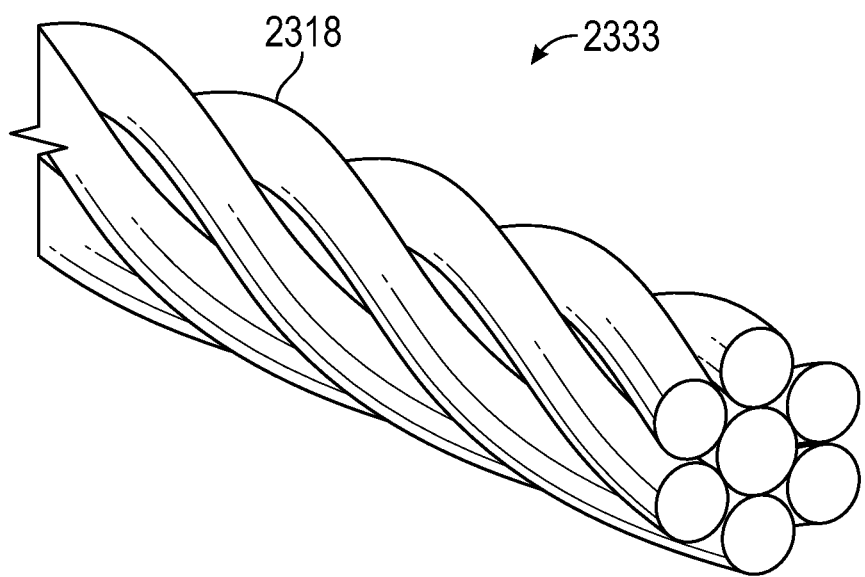
Figure 23C:
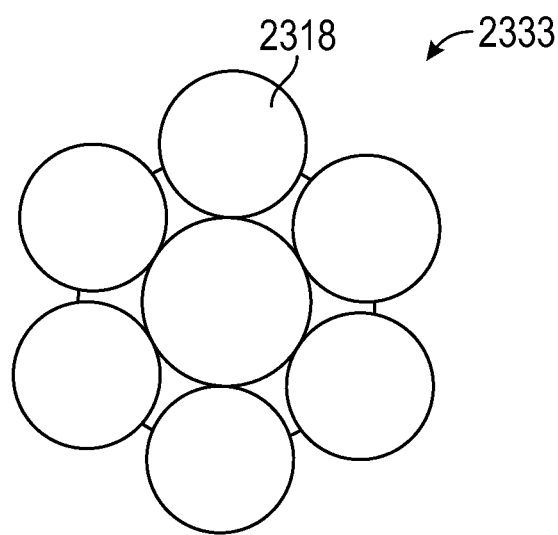

Referring to FIGS. 22A-22B, each strand 1833 can include a single filament 1818 (FIG. 22A) or multiple filaments 1818*a-c* (three filaments 1818*a-c* are shown in each strand 1833 in FIG. 22B). The filaments 1818 can be chosen (i.e., diameter, spacing, and modulus can be specifically tailored) to reduce crimp (the waviness or bending of the filaments). Reduced crimp can help the system provide enhanced compression buckling resistance, which can translate to enhanced system stiffness. Referring to FIGS. 23A-23C, each strand 2333 can include multiple filaments 2318 bundled together (i.e., that are twisted, woven, or braided). There can be, for example, 2-20 filaments 2318, such as 5-10 filaments 2318, such as 7 filaments (as shown in FIGS. 23A-23C). In some embodiments, each of the filaments 2318 can be 0.0005"-0.010", such as 0.001"-0.05", such as approximately 0.002" in diameter.

In some embodiments, the strands or filaments can be metal (e.g., stainless steel, aluminum, nitinol, tungsten, or titanium), plastic (nylon, polyethylene terephthalate, PEEK, polyetherimide), or high strength fiber (e.g., aramids, ultra-high molecular weight UHMW polyethylene, or liquid crystal polymers such as Vectran). In some embodiments, the strands can include filaments that are made of two or more different materials (e.g., some filaments in a strand can be nitinol and some stainless steel). In some embodiments, the strands or filaments can be made of a multi-layer composite, such as a metal core with a thin elastomeric, plastic, hard epoxy, or enamel coating. Coating the strands or filaments with a hard materials, such as hard epoxy or enamel, may in some embodiments help prevent yielding of the strands or filaments during use of the rigidizing device. In one specific example, the strands can include round nylon having a diameter of 0.010" (or metal filaments having a diameter of 0.003") intertwined with flat aluminized PET with cross-sectional dimensions of 0.002" by 0.002".

In some embodiments, the material for the strands of the braid can be a material with a known high coefficient of friction. For example, the strands can be a monolithic structure or have a coating such that the strands include aluminum on aluminum, copper on copper, silver on silver, or gold on gold. As another example, the strands can be coated with an elastomeric material (e.g., lower durometer elastomers can be coated on top of a higher modulus substrate). As another example, the strands can be made of styrene co-polymer, polycarbonate, or acrylic.

There can be between 12-800 strands in a braid layer, such as 24, 48, 96, 120, 144 or more strands extending within a braid layer. In some embodiments, there are 96 strands or more, 120 strands or more, 200 strands or more, or 240 strands or more. A higher number of strands may advantageously help rigidize the braid due to the increased interaction between strands.

In some embodiments, the braid layer can be integrated with or embedded into the matrix of any of the reinforced layers (e.g., innermost layer 8815).

Figure 17A:
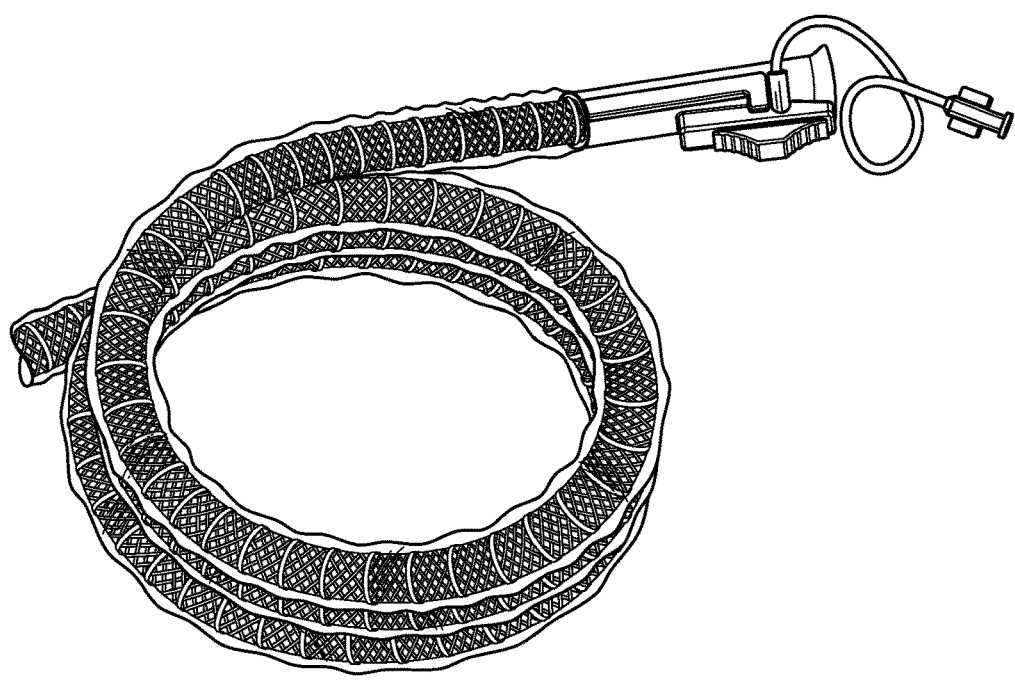
FIGS. 17A-17B show a rigidizing device in different rigidized shapes.
Figure 17B:
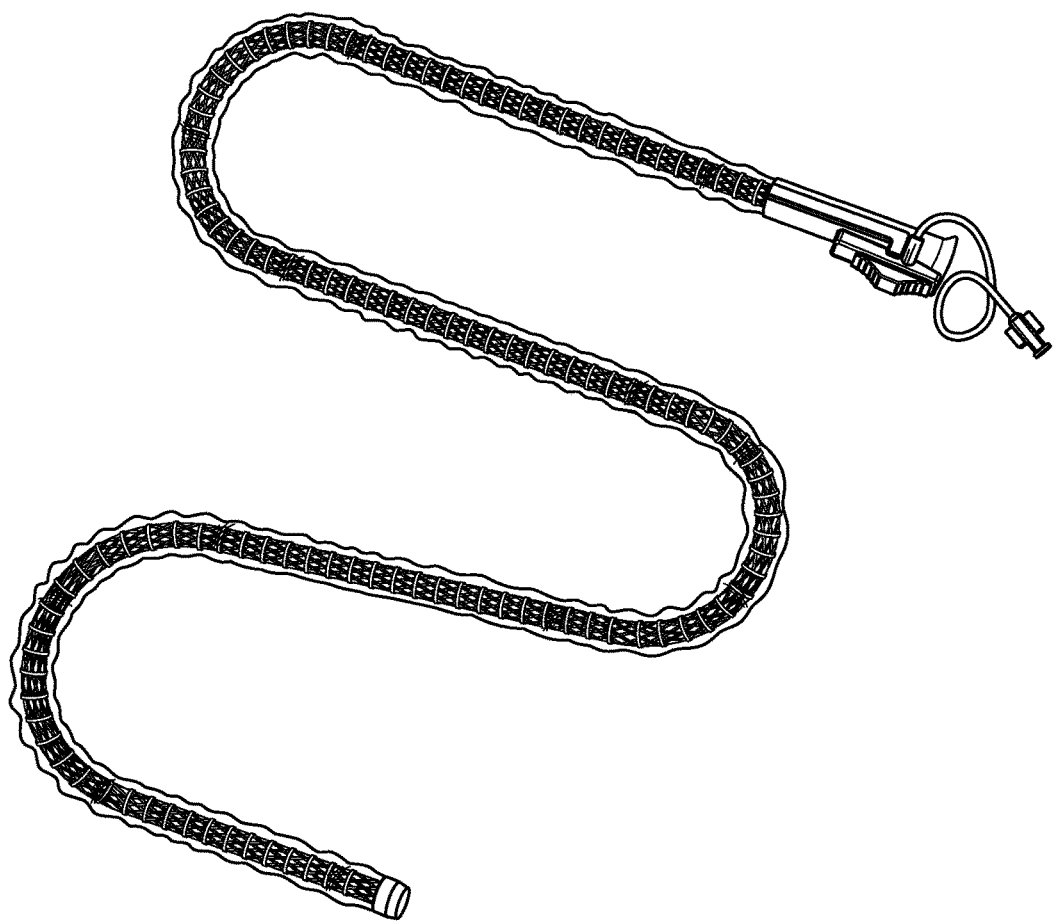

Exemplary rigidizing devices in the rigidized configuration are shown in FIGS. 17A and 17B. As the rigidizing device is rigidized, it does so in the shape it was in before vacuum or pressure was applied, i.e., it does not straighten, bend, or otherwise substantially modify its shape (e.g., it may stiffen in a looped configuration as shown in FIG. 17A or in a serpentine shape as shown in FIG. 17B). This can be because the air stiffening effect on the inner or outer layers (e.g., made of coil-wound tube) can be a small percentage (e.g., 5%) of the maximum load capability of the rigidizing device in bending, thereby allowing the rigidizing device to resist straightening. Upon release of the vacuum or pressure, braids or strands can unlock relative to one another and again move so as to allow bending of the rigidizing device. Again, as the rigidizing device is made more flexible through the release of vacuum or pressure, it does so in the shape it was in before the vacuum or pressure was released, i.e., it does not straighten, bend, or otherwise substantially modify its shape. Thus, the rigidizing devices described herein can transition from a flexible, less-stiff configuration to a rigid configuration of higher stiffness by restricting the motion between the strands of braid (e.g., by applying vacuum or pressure).

The rigidizing devices described herein can toggle between the rigid and flexible configurations quickly, and in some embodiments with an indefinite number of transition cycles. As interventional medical devices are made longer and inserted deeper into the human body, and as they are expected to do more exacting therapeutic procedures, there is an increased need for precision and control. Selectively rigidizing devices (e.g., overtubes) as described herein can advantageously provide both the benefits of flexibility (when needed) and the benefits of stiffness (when needed). Further, the rigidizing devices described herein can be used, for example, with classic endoscopes, colonoscopes, robotic systems, and/or navigation systems, such as those described in International Patent Application No. PCT/US2016/050290, filed Sep. 2, 2016, titled "DEVICE FOR ENDOSCOPIC ADVANCEMENT THROUGH THE SMALL INTESTINE," the entirety of which is incorporated by referenced herein.

The rigidizing devices described herein can additionally or alternatively include any of the features described with respect to International Patent Application No. PCT/US2016/050290, filed on Sep. 2, 2016, titled "DEVICE FOR ENDOSCOPIC ADVANCEMENT THROUGH THE SMALL INTESTINE," published as WO 2017/041052, International Patent Application No. PCT/US2018/042946, filed on Jul. 19, 2018, titled "DYNAMICALLY RIGIDIZING OVERTUBE," published as WO 2019/018682, International Patent Application No. PCT/US2019/042650, filed on Jul. 19, 2019, titled "DYNAMICALLY RIGIDIZING COMPOSITE MEDICAL STRUCTURES," published as WO 2020/018934, and International Patent Application No. PCT/US2020/013937 filed on Jan. 16, 2020, titled "DYNAMICALLY RIGIDIZING COMPOSITE MEDICAL STRUCTURES," the entireties of which are incorporated by reference herein.

The rigidizing devices described herein can be provided in multiple configurations, including different lengths and diameters. In some embodiments, the rigidizing devices can include working channels (for instance, for allowing the passage of typical endoscopic tools within the body of the rigidizing device), balloons, nested elements, and/or side-loading features.

Referring to FIGS. 18A-18D, in one embodiment, a tubular rigidizing device 100 can include a wall having a plurality of layers positioned around the lumen 120 (e.g., for placement of an instrument or endoscope therethrough). A vacuum can be supplied between the layers to rigidize the rigidizing device 100.

The innermost layer 115 can be configured to provide an inner surface against which the remaining layers can be consolidated, for example, when a vacuum is applied within the walls of the rigidizing device 100. The structure can be configured to minimize bend force/maximize flexibility in the non-vacuum condition. In some embodiments, the innermost layer 115 can include a reinforcement element 150z or coil within a matrix, as described above.

The layer 113 over (i.e., radially outwards of) the innermost layer 115 can be a slip layer.

The layer 111 can be a radial gap (i.e., a space). The gap layer 111 can provide space for the braided layer(s) thereover to move within (when no vacuum is applied) as well as space within which the braided or woven layers can move radially inward (upon application of vacuum).

The layer 109 can be a first braid layer including braided strands 133 similar to as described elsewhere herein. The braid layer can be, for example, 0.001" to 0.040" thick. For example, a braid layer can be 0.001", 0.003", 0.005", 0.010", 0.015", 0.020", 0.025" or 0.030" thick.

Figure 18A:
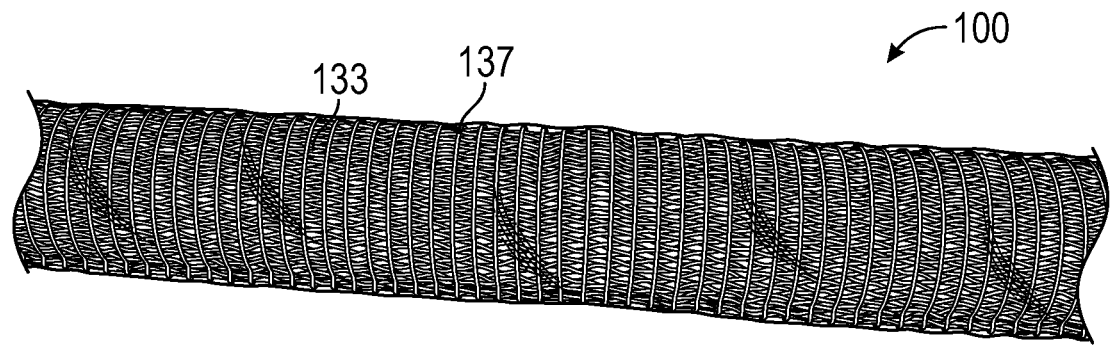
FIGS. 18A-18D show an exemplary vacuum rigidizing device.
Figure 18B:
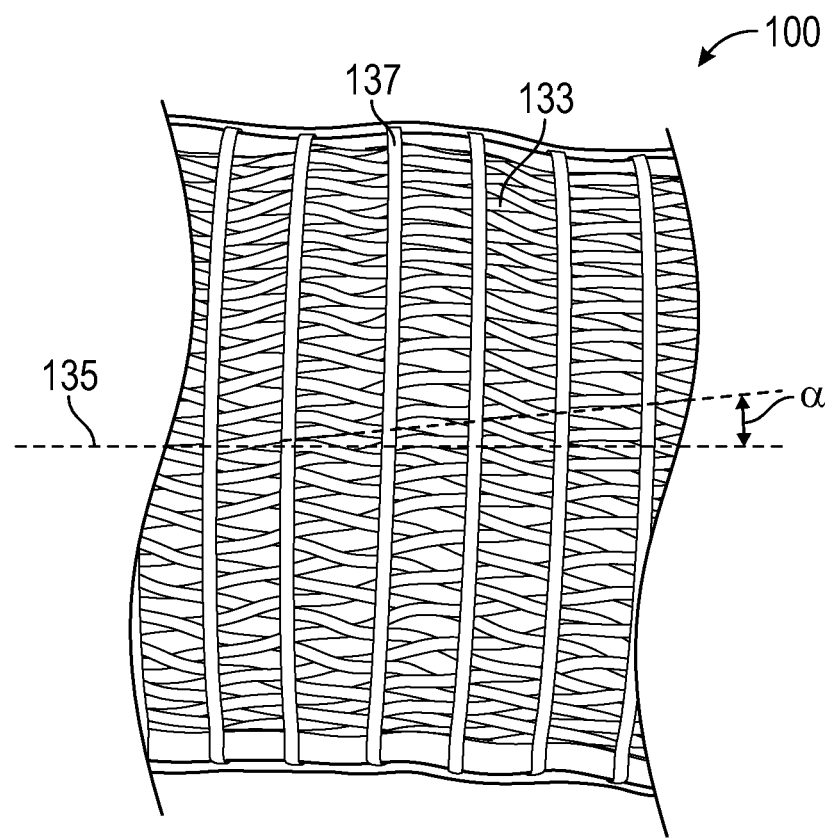

In some embodiments, as shown in FIG. 18B, the braid can have tensile or hoop fibers 137. Hoop fibers 137 can be spiraled and/or woven into a braid layer. Further, the hoop fibers 137 can be positioned at 2-50, e.g., 20-40 hoops per inch. The hoop fibers 137 can advantageously deliver high compression stiffness (to resist buckling or bowing out) in the radial direction, but can remain compliant in the direction of the longitudinal axis 135 of the rigidizing device 100. That is, if compression is applied to the rigidizing device 100, the braid layer 109 will try to expand in diameter as it compresses. The hoop fibers 137 can resist this diametrical expansion and thus resist compression. Accordingly, the hoop fiber 137 can provide a system that is flexible in bending but still resists both tension and compression.

The layer 107 can be another radial gap layer similar to layer 111.

Figure 18C:
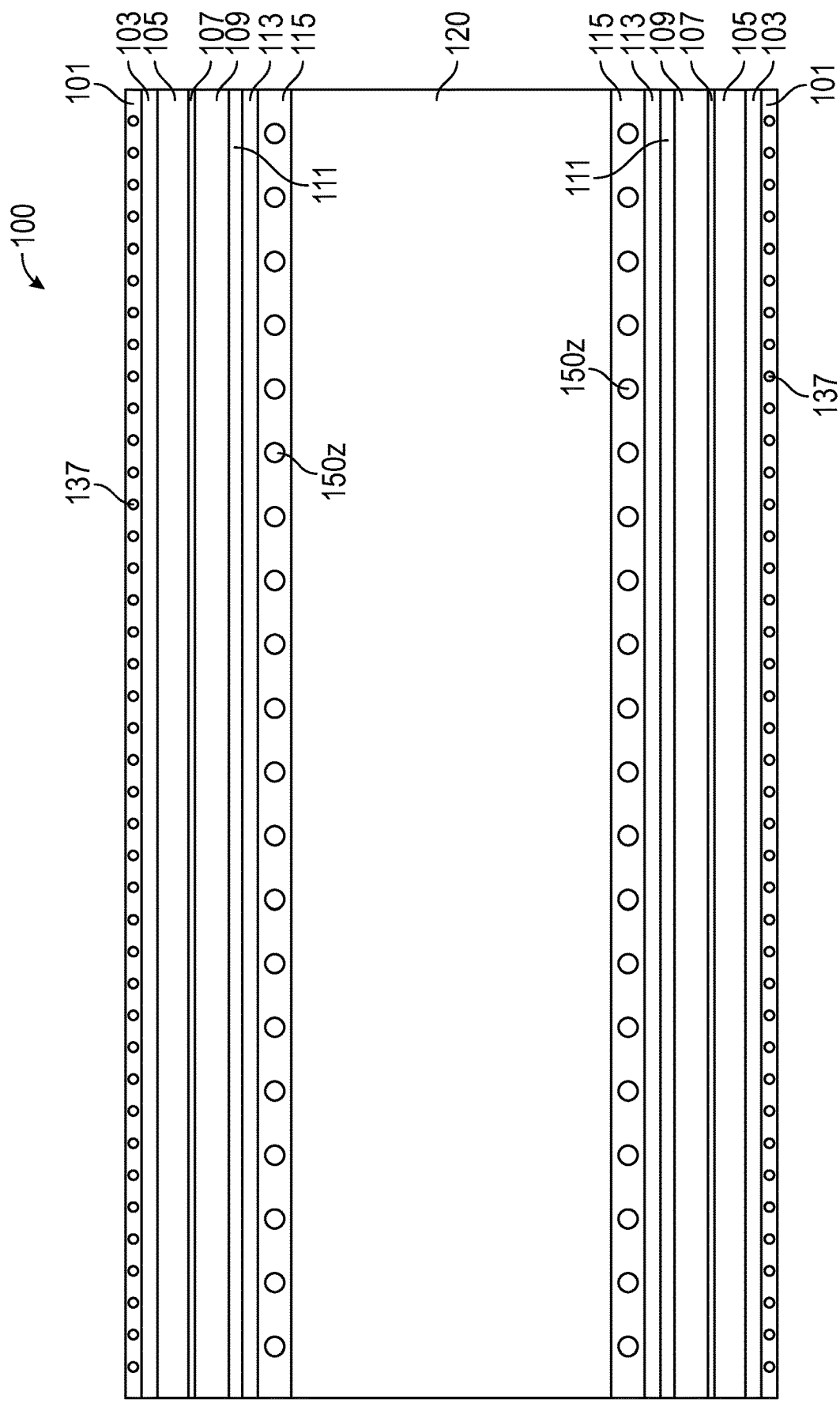
Figure 18D:
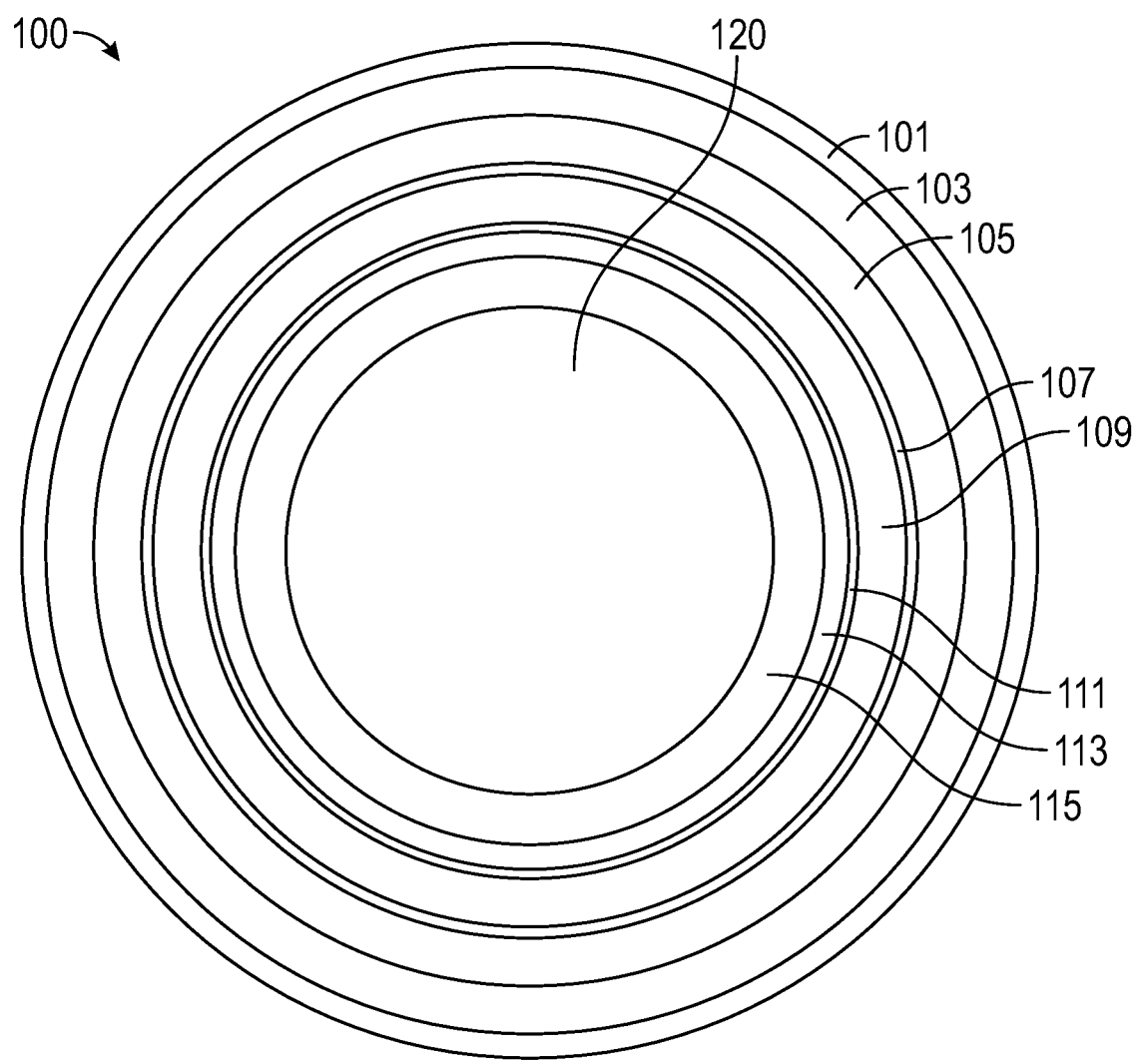

In some embodiments, the rigidizing devices described herein can have more than one braid layer. For example, the rigidizing devices can include two, three, or four braid layers. Referring to FIG. 18C, the layer 105 can be a second braid layer 105. The second braid layer 105 can have any of the characteristics described with respect to the first braid layer 109. In some embodiments, the braid of second braid layer 105 can be identical to the braid of first braid layer 109. In other embodiments, the braid of second braid layer 105 can be different than the braid of the first braid layer 109. For example, the braid of the second braid layer 105 can include fewer strands and have a larger braid angle α than the braid of the first braid layer 109. Having fewer strands can help increase the flexibility of the rigidizing device 100 (relative to having a second strand with equivalent or greater number of strands), and a larger braid angle α can help constrict the diameter of the of the first braid layer 109 (for instance, if the first braid layer is compressed) while increasing/maintaining the flexibility of the rigidizing device 100. As another example, the braid of the second braid layer 105 can include more strands and have a larger braid angle α than the braid of the first braid layer 109. Having more strands can result in a relatively tough and smooth layer while having a larger braid angle α can help constrict the diameter of the first braid layer 109.

The layer 103 can be another radial gap layer similar to layer 111. The gap layer 103 can have a thickness of 0.0002-0.04", such as approximately 0.03". A thickness within this range can ensure that the strands 133 of the braid layer(s) can easily slip and/or bulge relative to one another to ensure flexibility during bending of the rigidizing device 100.

The outermost layer 101 can be configured to move radially inward when a vacuum is applied to pull down against the braid layers 105, 109 and conform onto the surface(s) thereof. The outermost layer 101 can be soft and atraumatic and can be sealed at both ends to create a vacuum-tight chamber with layer 115. The outermost layer 101 can be elastomeric, e.g., made of urethane. The hardness of the outermost layer 101 can be, for example, 30 A to 80 A. Further, the outermost layer 101 can be have a thickness of 0.0001-0.01", such as approximately 0.001", 0.002, 0.003" or 0.004". Alternatively, the outermost layer can be plastic, including, for example, LDPE, nylon, or PEEK.

In some embodiments, the outermost layer 101 can, for example, have tensile or hoop fibers 137 extending therethrough. The hoop fibers 137 can be made, for example, of aramids (e.g., Technora, nylon, Kevlar), Vectran, Dyneema, carbon fiber, fiber glass or plastic. Further, the hoop fibers 137 can be positioned at 2-50, e.g., 20-40 hoops per inch. In some embodiments, the hoop fibers 137 can be laminated within an elastomeric sheath. The hoop fibers can advantageously deliver higher stiffness in one direction compared to another (e.g., can be very stiff in the hoop direction, but very compliant in the direction of the longitudinal axis of the rigidizing device). Additionally, the hoop fibers can advantageously provide low hoop stiffness until the fibers are placed under a tensile load, at which point the hoop fibers can suddenly exhibit high hoop stiffness.

In some embodiments, the outermost layer 101 can include a lubrication, coating and/or powder (e.g., talcum powder) on the outer surface thereof to improve sliding of the rigidizing device through the anatomy. The coating can be hydrophilic (e.g., a Hydromer® coating or a Surmodics® coating) or hydrophobic (e.g., a fluoropolymer). The coating can be applied, for example, by dipping, painting, or spraying the coating thereon.

The innermost layer 115 can similarly include a lubrication, coating (e.g., hydrophilic or hydrophobic coating), and/or powder (e.g., talcum powder) on the inner surface thereof configured to allow the bordering layers to more easily shear relative to each other, particularly when no vacuum is applied to the rigidizing device 100, to maximize flexibility.

In some embodiments, the outermost layer 101 can be loose over the radially inward layers. For instance, the inside diameter of layer 101 (assuming it constitutes a tube) may have a diametrical gap of 0"-0.200" with the next layer radially inwards (e.g., with a braid layer). This may give the vacuum rigidized system more flexibility when not under vacuum while still preserving a high rigidization multiple. In other embodiments, the outermost layer 101 may be stretched some over the next layer radially inwards (e.g., the braid layer). For instance, the zero-strain diameter of a tube constituting layer 101 may be from 0-0.200" smaller in diameter than the next layer radially inwards and then stretched thereover. When not under vacuum, this system may have less flexibility than one wherein the outer layer 101 is looser. However, it may also have a smoother outer appearance and be less likely to tear during use.

In some embodiments, the outermost layer 101 can be loose over the radially inward layers. A small positive pressure may be applied underneath the layer 101 in order to gently expand layer 101 and allow the rigidizing device to bend more freely in the flexible configuration. In this embodiment, the outermost layer 101 can be elastomeric and can maintain a compressive force over the braid, thereby imparting stiffness. Once positive pressure is supplied (enough to nominally expand the sheath off of the braid, for example, 2 psi), the outermost layer 101 is no longer is a contributor to stiffness, which can enhance baseline flexibility. Once rigidization is desired, positive pressure can be replaced by negative pressure (vacuum) to deliver stiffness.

A vacuum can be carried within rigidizing device 100 from minimal to full atmospheric vacuum (e.g., approximately 14.7 psi). In some embodiments, there can be a bleed valve, regulator, or pump control such that vacuum is bled down to any intermediate level to provide a variable stiffness capability. The vacuum pressure can advantageously be used to rigidize the rigidizing device structure by compressing the layer(s) of braided sleeve against neighboring layers. Braid is naturally flexible in bending (i.e. when bent normal to its longitudinal axis), and the lattice structure formed by the interlaced strands distort as the sleeve is bent in order for the braid to conform to the bent shape while resting on the inner layers. This results in lattice geometries where the corner angles of each lattice element change as the braided sleeve bends. When compressed between conformal materials, such as the layers described herein, the lattice elements become locked at their current angles and have enhanced capability to resist deformation upon application of vacuum, thereby rigidizing the entire structure in bending when vacuum is applied. Further, in some embodiments, the hoop fibers through or over the braid can carry tensile loads that help to prevent local buckling of the braid at high applied bending load.

The stiffness of the rigidizing device 100 can increase from 2-fold to over 30-fold, for instance 10-fold, 15-fold, or 20-fold, when transitioned from the flexible configuration to the rigid configuration. In one specific example, the stiffness of a rigidizing device similar to rigidizing device 100 was tested. The wall thickness of the test rigidizing device was 1.0 mm, the outer diameter was 17 mm, and a force was applied at the end of a 9.5 cm long cantilevered portion of the rigidizing device until the rigidizing device deflected 10 degrees. The forced required to do so when in flexible mode was only 30 grams while the forced required to do so in rigid (vacuum) mode was 350 grams.

In some embodiments of a vacuum rigidizing device 100, there can be only one braid layer. In other embodiments of a vacuum rigidizing device 100, there can be two, three, or more braid layers. In some embodiments, one or more of the radial gap layers or slip layers of rigidizing device 100 can be removed. In some embodiments, some or all of the slip layers of the rigidizing device 100 can be removed.

The braid layers described herein can act as a variable stiffness layer. The variable stiffness layer can include one or more variable stiffness elements or structures that, when activated (e.g., when vacuum is applied), the bending stiffness and/or shear resistance is increased, resulting in higher rigidity. Other variable stiffness elements can be used in addition to or in place of the braid layer. In some embodiments, engagers can be used as a variable stiffness element, as described in International Patent Application No. PCT/US2018/042946, filed Jul. 19, 2018, titled "DYNAMICALLY RIGIDIZING OVERTUBE," the entirety of which is incorporated by reference herein. Alternatively or additionally, the variable stiffness element can include particles or granules, jamming layers, scales, rigidizing axial members, rigidizers, longitudinal members or substantially longitudinal members.

Figure 19B:
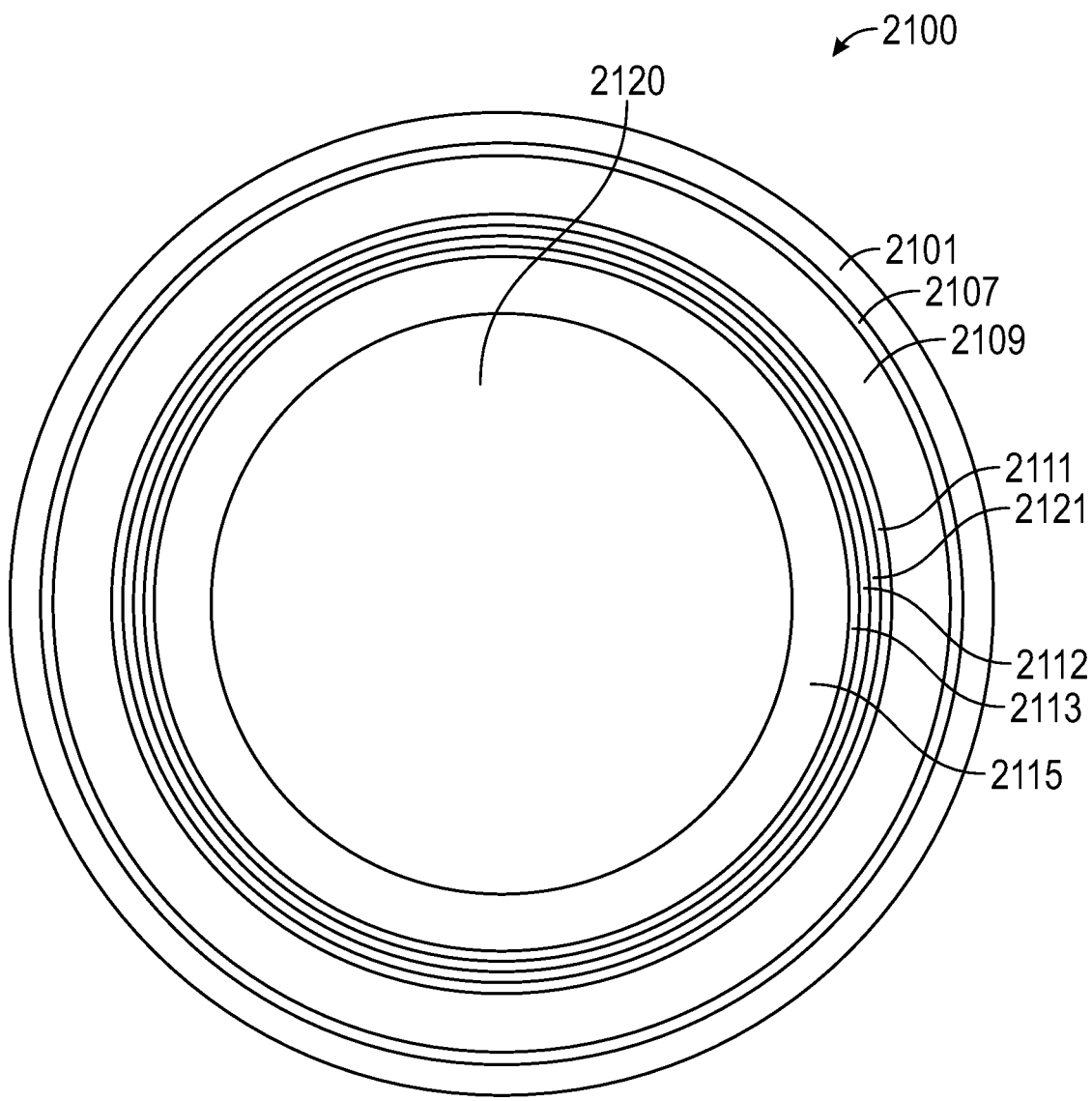

In some embodiments, the rigidizing devices described herein can rigidize through the application of pressure rather than vacuum. For example, referring to FIGS. 19A-19B, the rigidizing device 2100 can be similar to rigidizing device 100 except that it can be configured to hold pressure (e.g., of greater than 1 atm) therein for rigidization rather than vacuum. The rigidizing device 2100 can thus include a plurality of layers positioned around the lumen 2120 (e.g., for placement of an instrument or endoscope therethrough). The rigidizing device 2100 can include an innermost layer 2115 (similar to innermost layer 115), a slip layer 2113 (similar to slip layer 113), a pressure gap 2112, a bladder layer 2121, a gap layer 2111 (similar to gap layer 111), a braid layer 2109 (similar to braid layer 109) or other variable stiffness layer as described herein, a gap layer 2107 (similar to layer 107), and an outermost containment layer 2101.

The pressure gap 2112 can be a sealed chamber that provides a gap for the application of pressure to layers of rigidizing device 2100. The pressure can be supplied to the pressure gap 2112 using a fluid or gas inflation/pressure media. The inflation/pressure media can be water or saline or, for example, a lubricating fluid such as soil or glycerin. The lubricating fluid can, for example, help the layers of the rigidizing device 2100 flow over one another in the flexible configuration. The inflation/pressure media can be supplied to the gap 2112 during rigidization of the rigidizing device 2100 and can be partially or fully evacuated therefrom to transform the rigidizing device 2100 back to the flexible configuration. In some embodiments, the pressure gap 2112 of the rigidizing device 2100 can be connected to a pre-filled pressure source, such as a pre-filled syringe or a pre-filled insufflator, thereby reducing the physician's required set-up time.

The bladder layer 2121 can be made, for example, of a low durometer elastomer (e.g., of shore 20 A to 70 A) or a thin plastic sheet. The bladder layer 2121 can be formed out of a thin sheet of plastic or rubber that has been sealed lengthwise to form a tube. The lengthwise seal can be, for instance, a butt or lap joint. For instance, a lap joint can be formed in a lengthwise fashion in a sheet of rubber by melting the rubber at the lap joint or by using an adhesive. In some embodiments, the bladder layer 2121 can be 0.0002-0.020" thick, such as approximately 0.005" thick. The bladder layer 2121 can be soft, high-friction, stretchy, and/or able to wrinkle easily. In some embodiments, the bladder layer 2121 is a polyolefin or a PET. The bladder 2121 can be formed, for example, by using methods used to form heat shrink tubing, such as extrusion of a base material and then wall thinning with heat, pressure and/or radiation. When pressure is supplied through the pressure gap 2112, the bladder layer 2121 can expand through the gap layer 2111 to push the braid layer 2109 against the outermost containment layer 2101 such that the relative motion of the braid strands is reduced.

The outermost containment layer 2101 can be a tube, such as an extruded tube. Alternatively, the outermost containment layer 2101 can be a tube in which a reinforcing member (for example, metal wire, including round or rectangular cross-sections) is encapsulated within an elastomeric matrix, similar to as described with respect to the innermost layer for other embodiments described herein. In some embodiments, the outermost containment layer 2101 can include a helical spring (e.g., made of circular or flat wire), and/or a tubular braid (such as one made from round or flat metal wire) and a thin elastomeric sheet that is not bonded to the other elements in the layer. The outermost containment layer 2101 can be a tubular structure with a continuous and smooth surface. This can facilitate an outer member that slides against it in close proximity and with locally high contact loads (e.g., a nested configuration as described further herein). Further, the outer layer 2101 can be configured to support compressive loads, such as pinching. Additionally, the outer layer 2101 (e.g., with a reinforcement element therein) can be configured to prevent the rigidizing device 2100 from changing diameter even when pressure is applied.

Because both the outer layer 2101 and the inner layer 2115 include reinforcement elements therein, the braid layer 2109 can be reasonably constrained from both shrinking diameter (under tensile loads) and growing in diameter (under compression loads).

Figure 20:
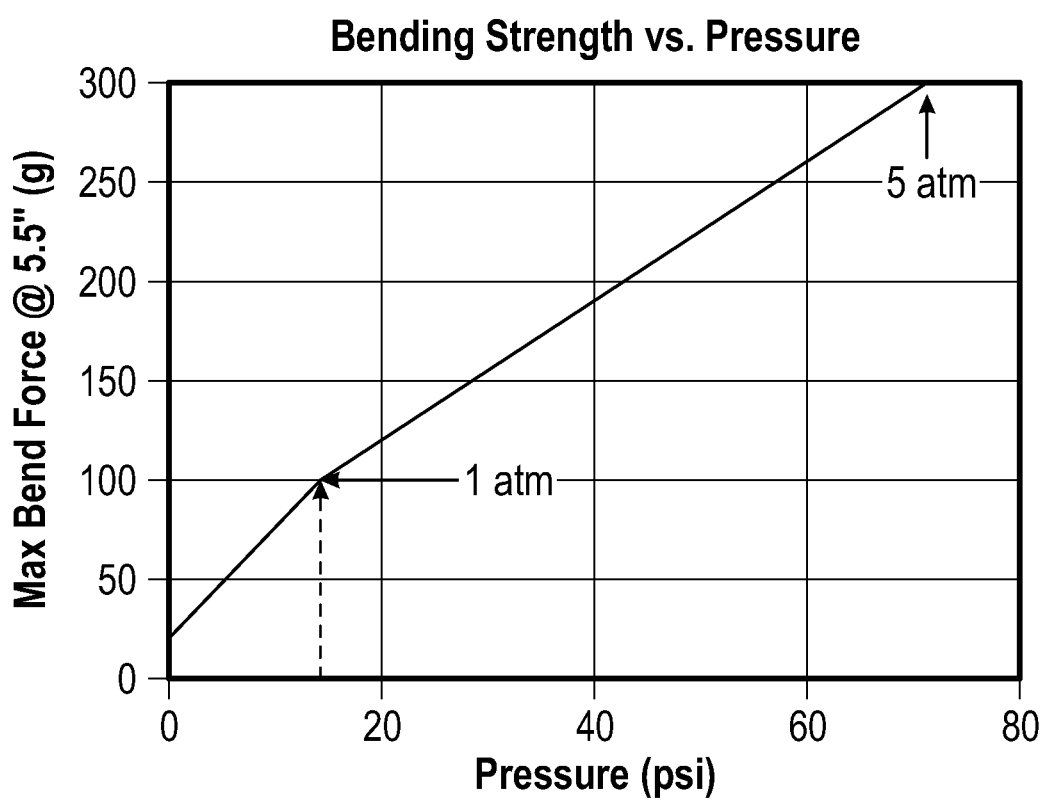
FIG. 20 is a graph of bending strength vs pressure for a rigidizing device.

By using pressure rather than vacuum to transition from the flexible state to the rigid state, the rigidity of the rigidizing device 2100 can be increased. For example, in some embodiments, the pressure supplied to the pressure gap 2112 can be between 1 and 40 atmospheres, such as between 2 and 40 atmospheres, such as between 4 and 20 atmospheres, such as between 5 and 10 atmospheres. In some embodiments, the pressure supplied is approximate 2 atm, approximately 4 atmospheres, approximately 5 atmospheres, approximately 10 atmospheres, approximately 20 atmospheres. In some embodiments, the rigidizing device 2100 can exhibit change in relative bending stiffness (as measured in a simple cantilevered configuration) from the flexible configuration to the rigid configuration of 2-100 times, such as 10-80 times, such as 20-50 times. For example, the rigidizing device 2100 can have a change in relative bending stiffness from the flexible configuration to the rigid configuration of approximately 10, 15, 20, or 25, 30, 40, 50, or over 100 times. FIG. 20 shows a graph of bending strength vs pressure for a rigidizing device as described herein. As shown, the bending strength of the rigidizing device increases as the pressure supplied to the wall increases.

Advantageously, the inner layers with sublayers and/or overlapping reinforcement elements described herein can be flexible, but resist a high pressure (e.g., pressure acting on the inner layer's outer diameter that may otherwise make the tube collapse). Additionally, the inner layers with sublayers and/or overlapping reinforcement elements described herein can advantageously provide enhanced torque carrying capacity or torsional stiffness.

It should be understood that any feature described herein with respect to one embodiment can be combined with or substituted for any feature described herein with respect to another embodiment. For example, the various layers and/or features of the rigidizing devices described herein can be combined, substituted, and/or rearranged relative to other layers.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are a plurality of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

What is claimed is:

1. A rigidizing device comprising:
   an elongate flexible tube, wherein the elongate flexible tube comprises a first reinforcement element and second reinforcement element, and wherein the second reinforcement element is counterwound relative to the first reinforcement element;
   a binding layer between the first reinforcement element and the second reinforcement element;
   a stiffening layer positioned radially outwards of the elongate flexible tube;
   an outer layer over the elongate flexible tube and the stiffening layer; and
   a vacuum or pressure inlet between the elongate flexible tube and the outer layer and configured to attach to a source of vacuum or pressure;
   wherein the rigidizing device is configured to have a rigid configuration when vacuum or pressure is applied through the inlet and a flexible configuration when vacuum or pressure is not applied through the inlet.

2. The rigidizing device of claim 1, wherein the binding layer comprises an adhesive.

3. The rigidizing device of claim 1, wherein the first and second reinforcement elements are embedded in a matrix, and wherein the binding layer comprises a same material as the matrix.

4. The rigidizing device of claim 1, wherein the stiffening layer is a braid layer.

5. The rigidizing device of claim 1, wherein the first reinforcement element is wound at an angle in a positive direction and the second reinforcement angle is wound at the same angle in a negative direction.

6. The rigidizing device of claim 1, wherein the first reinforcement element or the second reinforcement element is wound at an angle of greater than 60 degrees and less than 90 degrees relative to a longitudinal axis of the rigidizing device.

7. The rigidizing device of claim 1, wherein the first and second reinforcement elements are woven together.

8. A rigidizing device comprising:
   an elongate flexible tube, wherein the elongate flexible tube comprises a first reinforcement element and second reinforcement element, and wherein the second reinforcement element is counterwound relative to the first reinforcement element, further wherein the first reinforcement element is positioned radially outwards of the second reinforcement element;
   a separating layer between the first reinforcement element and the second reinforcement element;
   a stiffening layer positioned radially outwards of the elongate flexible tube;
   an outer layer over the elongate flexible tube and the stiffening layer; and
   a vacuum or pressure inlet between the elongate flexible tube and the outer layer and configured to attach to a source of vacuum or pressure;
   wherein the rigidizing device is configured to have a rigid configuration when vacuum or pressure is applied through the inlet and a flexible configuration when vacuum or pressure is not applied through the inlet.

9. A rigidizing device comprising:
   an elongate flexible tube, wherein the elongate flexible tube comprises a first sublayer and a second sublayer, wherein the first sublayer comprises a first reinforcement element forming a first spiral about a longitudinal axis of the rigidizing device, and wherein the second sublayer comprises a second reinforcement element forming a second spiral about the longitudinal axis, wherein the second spiral is positioned over spaces between windings of the first spiral;
   a binding layer between the first sublayer and the second sublayer;
   a stiffening layer positioned radially outwards of the elongate flexible tube;
   an outer layer over the elongate flexible tube and the stiffening layer; and
   a vacuum or pressure inlet between the elongate flexible tube and the outer layer and configured to attach to a source of vacuum or pressure;
   wherein the rigidizing device is configured to have a rigid configuration when vacuum or pressure is applied through the inlet and a flexible configuration when vacuum or pressure is not applied through the inlet.

10. The rigidizing device of claim 9, wherein the binding layer comprises an adhesive.

11. The rigidizing device of claim 9, wherein the first and second reinforcement elements are embedded in a matrix, and wherein the binding layer comprises a same material as the matrix.

12. The rigidizing device of claim 9, wherein the stiffening layer is a braid layer.

13. The rigidizing device of claim 9, wherein the first reinforcement element is wound at a same direction and at a same pitch as the second reinforcement element.

14. The rigidizing device of claim 9, wherein the first reinforcement element and the second reinforcement element are each wound at an angle of greater than 60 degrees and less than 90 degrees relative to a longitudinal axis of the rigidizing device.

15. The rigidizing device of claim 9, wherein the second reinforcement element radially overlaps at least a portion of the first reinforcement element.

16. The rigidizing device of claim 9, wherein the second reinforcement element has a width that is 1.5-4 times a width of the spaces between the first spiral.

17. The rigidizing device of claim 9, wherein the second reinforcement element has a width that is smaller than a width of the first reinforcement element.

* * * * *